US011176318B2

(12) United States Patent
Carbonell et al.

(10) Patent No.: US 11,176,318 B2
(45) Date of Patent: Nov. 16, 2021

(54) MEDICAL NETWORK

(71) Applicant: INTERNATIONAL BUSINESS MACHINES CORPORATION, Armonk, NY (US)

(72) Inventors: Lee A. Carbonell, Flower Mound, TX (US); Tsz Shing Cheng, Grand Prairie, TX (US); Jeffrey L. Edgington, Keller, TX (US); Pandian Mariadoss, Allen, TX (US)

(73) Assignee: International Business Machines Corporation, Armonk, NY (US)

( * ) Notice: Subject to any disclaimer, the term of this patent is extended or adjusted under 35 U.S.C. 154(b) by 888 days.

(21) Appl. No.: 15/599,028

(22) Filed: May 18, 2017

(65) Prior Publication Data
US 2018/0336317 A1  Nov. 22, 2018

(51) Int. Cl.
*G06Q 30/02* (2012.01)
*G16H 80/00* (2018.01)
(Continued)

(52) U.S. Cl.
CPC ........ *G06F 40/20* (2020.01); *G06F 16/24578* (2019.01); *G06F 16/93* (2019.01);
(Continued)

(58) Field of Classification Search
CPC ........ G16H 80/00; G16H 50/70; G16H 15/00; G16H 40/20; G16H 10/60; G16H 50/00;
(Continued)

(56) References Cited

U.S. PATENT DOCUMENTS 6,648,820 B1  11/2003  Sarel
7,289,844 B2  10/2007  Misczynski
(Continued)

FOREIGN PATENT DOCUMENTS

WO  2002001470 A1  1/2002
WO  2007072425 A2  6/2007
(Continued)

OTHER PUBLICATIONS

Chan, Amanda; Doctor Will Skype You Now: More MDs Use Web for House Calls; LiveScience; Jan. 2, 2011; 6 pages.
(Continued)

*Primary Examiner* — Eliza A Lam
(74) *Attorney, Agent, or Firm* — Schmeiser, Olsen & Watts, LLP; Aaron Pontikos

(57) ABSTRACT

Systems and tools for sharing medical costs between prospective patients seeking treatment, and existing patients of a medical network. Prospective patients may actively query medical costs for specific conditions and treatments for the specific conditions previously experienced by existing patients. Existing patients contributing to the documents accessible by the medical network may upload anonymous versions of EOBs, medical bills and medical documents to the medical network in exchange for rewards. The prospective patients may communicate and query the desired information using natural language inputs to instruct a client computing system to search the medical network for relevant treatment information. The prospective patient may use natural language commands or other inputs to filter the query results by condition, location, cost, quality of service, service provider, insurance provider, or any other parameter that may be detailed by the medical documents accessible through the medical network.

12 Claims, 11 Drawing Sheets

(51) Int. Cl.
| | |
|---|---|
| *G16H 10/60* | (2018.01) |
| *G06F 40/20* | (2020.01) |
| *G16H 50/00* | (2018.01) |
| *G06Q 20/22* | (2012.01) |
| *G06F 16/93* | (2019.01) |
| *G06F 16/9535* | (2019.01) |
| *G06F 16/2457* | (2019.01) |
| *G16H 40/20* | (2018.01) |
| *G06F 40/30* | (2020.01) |
| *G06F 40/117* | (2020.01) |
| *G16H 15/00* | (2018.01) |
| *G16H 50/70* | (2018.01) |

(52) U.S. Cl.
CPC ........ *G06F 16/9535* (2019.01); *G06F 40/117* (2020.01); *G06F 40/30* (2020.01); *G06Q 20/29* (2013.01); *G06Q 30/0233* (2013.01); *G16H 10/60* (2018.01); *G16H 40/20* (2018.01); *G16H 50/00* (2018.01); *G16H 80/00* (2018.01); *G16H 15/00* (2018.01); *G16H 50/70* (2018.01)

(58) Field of Classification Search
CPC .. G06Q 20/29; G06Q 30/0233; G06F 17/218; G06F 17/27; G06F 16/24578; G06F 16/9535; G06F 16/93; G06F 19/328; G06F 19/325; G06F 17/2785
See application file for complete search history.

(56) References Cited

U.S. PATENT DOCUMENTS

| | | | | |
|---|---|---|---|---|
| 7,404,007 | B2* | 7/2008 | Wilcock | G06Q 30/02 709/213 |
| 7,490,046 | B1 | 2/2009 | Wyatt | |
| 8,527,292 | B1* | 9/2013 | Ozden | G06Q 30/04 705/2 |
| 8,548,937 | B2 | 10/2013 | Saigal | |
| 8,684,920 | B2 | 4/2014 | Houben | |
| 8,845,535 | B2 | 9/2014 | Pinedo | |
| 8,930,224 | B2 | 1/2015 | Heywood | |
| 9,219,660 | B2* | 12/2015 | Sanches | H04L 41/026 |
| 9,418,150 | B2 | 8/2016 | Charlot | |
| 2004/0172291 | A1 | 9/2004 | Knowlton | |
| 2006/0100904 | A1 | 5/2006 | Jee | |
| 2007/0250342 | A1 | 10/2007 | Sohal | |
| 2007/0250343 | A1 | 10/2007 | Sohal | |
| 2008/0133272 | A1 | 6/2008 | Marshall | |
| 2009/0177495 | A1 | 7/2009 | Abousy | |
| 2010/0262436 | A1 | 10/2010 | Chen et al. | |
| 2011/0225526 | A1* | 9/2011 | Baret | G06Q 10/10 715/764 |
| 2012/0047105 | A1 | 2/2012 | Saigal | |
| 2012/0173475 | A1 | 7/2012 | Ash et al. | |
| 2013/0150711 | A1 | 6/2013 | Theobold | |
| 2014/0074976 | A1 | 3/2014 | Greenberg et al. | |
| 2014/0204118 | A1 | 7/2014 | Berry | |
| 2014/0207631 | A1* | 7/2014 | Fisher | G06Q 40/10 705/30 |
| 2014/0244291 | A1 | 8/2014 | Bonner | |
| 2014/0244292 | A1* | 8/2014 | Rosenberg | G16H 70/00 705/2 |
| 2014/0276096 | A1 | 9/2014 | Bonutti | |
| 2015/0012631 | A1 | 1/2015 | Udani et al. | |
| 2017/0124258 | A1* | 5/2017 | Fritsch | G16H 50/70 |
| 2018/0025075 | A1* | 1/2018 | Beller | G06F 40/284 707/769 |

FOREIGN PATENT DOCUMENTS

| | | |
|---|---|---|
| WO | 2012154672 A2 | 11/2012 |
| WO | 2014124289 A1 | 8/2014 |

OTHER PUBLICATIONS

Compare Health Costs & Quality of Care in New Hampshire; http://nhhealthcost.nh.gov/insured; retrieved from the Internet Jul. 24, 2021; 3 pages.

Estimate Costs; Fair Health; http://fairhelthconsumer.org/medicalcostlookup.php; retrieved from the Internet Jul. 24, 2021; 1 page.

Find an Urgent Care Clinic Near You; CareNow Markets; http://web.archive.org/web/20161120025104/http://ww.carenow.com:80/;; retrieved from the Internet Jul. 24, 2021; 3 pages.

Google Play; Doctor on Demand; retrieved from the Internet Dec. 2016; 3 pages.

Health In Reach search; https://www.healthinreach.com/search/; retrieved from the Internet Jul. 24, 2021; 2 pages.

Luthra, Shefali; Consumers still struggling with medical debt; USA Today; Feb. 1, 2015; 3 pages.

Medical Bill Exchange; http://www.medicalbillexchange.com/; retrieved from the Internet Jul. 24, 2021; 2 pages.

Medical Procedure & Facility Cost, Procedure Information for Patients; New Choice Health; http://www.newchoicehealth.com/; retrieved from the Internet Jul. 24, 2021; 6 pages.

Mell, Peter et al.; "The NIST Definition of Cloud Computing;" National Institute of Standards and Technology; Special Publication 800-145; Sep. 2011; 7 pages.

Surgery Center of Oklahoma; http://surgerycenterok.com/pricing/; retrieved from the Internet Jul. 24, 2021; 100 pages.

Test reports in the Field of Health, Fitness and Medicine; https://cakehealth.com/; retrieved from the Internet Jul. 24, 2021; 4 pages.

That CT scan costs how much: Health-care prices are all over the map, even within your plan's network; Consumer Reports magazine; Jul. 2012; 5 pages.

The true quality and cost of healthcare is right in front of you; Healthcare Bluebook; https://healthcarebluebook.com retrieved from the Internet Jul. 24, 2021; 5 pages.

The world's most innovative brands choose LivePerson's Conversational Cloud; www.liveperson.com; retrieved from the Internet Jul. 24, 2021; 7 pages.

United Healthcare; My Healthcare Cost Estimator; http://www.uhc.com/individual-and-family/why-uhc/programs-tools/myhealthcare-cost-estimator; retrieved from the Internet Jul. 24, 2021; 2 pages.

Urgent Care of Emergency Room? What's the Difference? http://web.archive.org/web/20161105163617/http://medspring.com; retrieved from the Internet; Jul. 24, 2021; 3 pages.

Zamosky, Lisa; New tools make it easier to find prices for medical procedures; LA Times; http://articles.latimes.com/2013/mar/22/business/la-fi-healthcare-watch-20130324; Mar. 22, 2013; 14 pages.

* cited by examiner

MEDICAL NETWORK

TECHNICAL FIELD

The present disclosure relates generally toward computer systems, methods and tools of a user-guided medical network.

BACKGROUND

In the United States, medical care costs are often very high and unpredictable. The costs for a particular treatment or procedure may vary wildly depending on numerous factors surrounding the patient, treatment location, doctors and insurers. Even with insurance coverage, medical consumers are often shocked with the costs presented in the form of soaring medical bills, expensive deductibles, donuthole coverages and high out of pocket maximums. Moreover, estimating the costs for medical procedures from the initial starting point to the conclusion of the treatment can be very difficult obtain before committing to a particular course of medical care.

Several reasons can be attributed to why medical costs are unpredictable and thus making estimating or comparing medical costs difficult to achieve. First, unlike other products and services where cost estimates are typically provided in advance, costs for medical procedures, services, facilities and supplies are largely unknown. Medical providers, such as hospitals do not make pricing information available or publish prices in an easily accessible location. Moreover, not only are the costs of individual actions (identified by medical codes) largely unknown to medical consumers, but the actual medical codes used for the treatment of the medical consumer may not even be determined by the insurance or medical provider until the procedures and services are performed. Furthermore, medical providers of the treatment may not be known to the medical consumer prior to the services being provided. For example, treatment options may change or additional personnel may be utilized such as an anesthesiologist or emergency room doctors. Moreover, additional costs may be added on afterward or adjusted based on the progress of the patient. For instance, follow up visits, supplies, services and secondary procedures.

SUMMARY

A first embodiment of the present disclosure provides a method for sharing medical costs to a medical network comprising the steps of: accessing, by a computer system, a portal to the medical network; inputting, by the computer system, a natural language command instructing an upload of an explanation of benefits (EOB) document to the medical network; digitizing, by the computer system, the EOB document; converting, by the computer system, text displayed by the EOB document to machine encoded text; tagging, by the computer system, identifying properties of the EOB document; anonymizing, by the computer system, confidential patient information provided within the EOB document; uploading, by the computer system, a tagged EOB document to the medical network; and receiving, by the computer system, reward points in exchanged for the tagged EOB document uploaded to the medical network.

A second embodiment of the present disclosure provides a computer system comprising a processor; a memory device coupled to the processor; and a computer readable storage device coupled to the processor, wherein the storage device contains program code executable by the processor via the memory device to implement a method for sharing medical costs to a medical network comprising the steps of: accessing, by the computer system, a portal to the medical network; inputting, by the computer system, a natural language command instructing an upload of an explanation of benefits (EOB) document to the medical network; digitizing, by the computer system, the EOB document; converting, by the computer system, text displayed by the EOB document to machine encoded text; tagging, by the computer system, identifying properties of the EOB document; anonymizing, by the computer system, confidential patient information provided within the EOB document; uploading, by the computer system, a tagged EOB document to the medical network; and receiving, by the computer system, reward points in exchanged for the tagged EOB document uploaded to the medical network.

A third embodiment of the present disclosure provides a computer program product comprising: one or more computer readable hardware storage devices having computer readable program code stored therein, said program code containing instructions executable by one or more processors to implement a method for sharing medical costs comprising the steps of: accessing, by a computer system, a portal to the medical network; inputting, by the computer system, a natural language command instructing an upload of an explanation of benefits (EOB) document to the medical network; digitizing, by the computer system, the EOB document; converting, by the computer system, text displayed by the EOB document to machine encoded text; tagging, by the computer system, identifying properties of the EOB document; anonymizing, by the computer system, confidential patient information provided within the EOB document; uploading, by the computer system, a tagged EOB document to the medical network; and receiving, by the computer system, reward points in exchanged for the tagged EOB document uploaded to the medical network.

DETAILED DESCRIPTION

Figure 1:
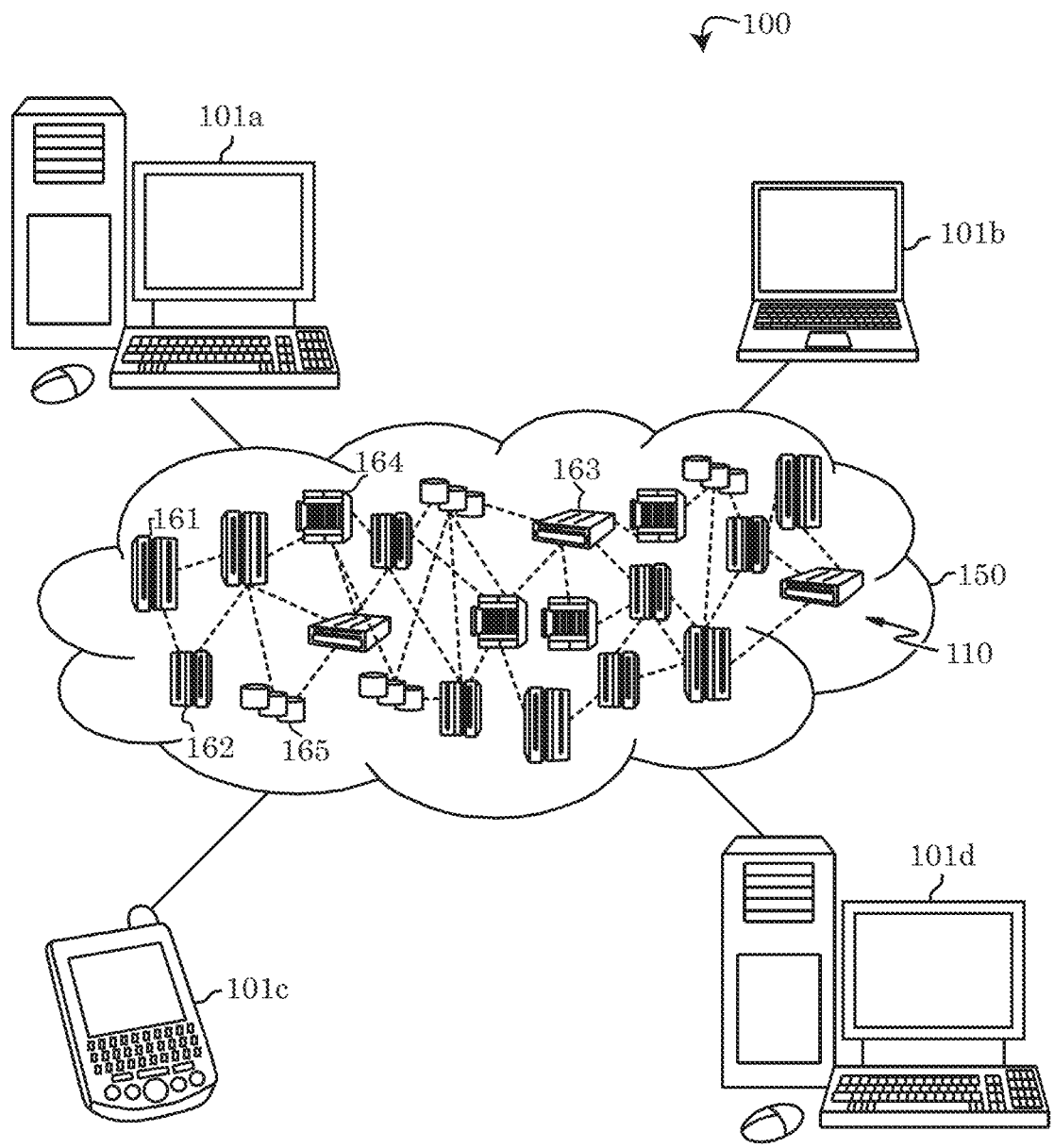
FIG. 1 depicts a diagram of an embodiment of a cloud computing environment for sharing medical costs to a medical network.

Although certain embodiments are shown and described in detail, it should be understood that various changes and modifications may be made without departing from the scope of the appended claims. The scope of the present disclosure will in no way be limited to the number of constituting components, the materials thereof, the shapes thereof, the relative arrangement thereof, etc., and are disclosed simply as an example of embodiments of the present disclosure. A more complete understanding of the present embodiments and advantages thereof may be acquired by referring to the following description taken in conjunction with the accompanying drawings, in which like reference numbers indicate like features.

As a preface to the detailed description, it should be noted that, as used in this specification and the appended claims, the singular forms "a", "an" and "the" include plural referents, unless the context clearly dictates otherwise.

Overview

Existing tools and websites have been created to assist medical consumers with predicting cost estimates for medical treatment and services. The existing tools often only provide a generic cost estimate or a "fair" market estimate of prices for individual procedures that a medical consumer may expect. Often, the existing tools and websites are inexact, resulting in the actual medical costs incurred by a customer that can be quite significantly different from the cost estimate provided by existing tools and websites.

Several challenges may still remain for medical consumers who attempt to estimate medical costs using the currently available systems, tools, methods and websites for estimating medical costs. First, the currently available resources may not link together individual billings and EOBs, making calculations of total costs for a treatment from beginning to end exceptionally difficult identify. A full picture of the total treatment costs may not be readily available. Second, existing tools and other resources may make cost comparisons and estimations difficult for comparing actual costs against the estimated "fair" costs for treating a particular medical condition. Third, existing tools and systems for estimating costs may not provide any context behind a rating associated with actual medical treatments received by medical consumers. For example, existing estimation resources are unable to identify extenuating circumstances, reasons for selecting a particular provider, occurrence of a second opinion or referrals. Moreover, due to particular laws such as HIPPA, it can be difficult to obtain EOBs and medical bills that are anonymous. The medical documents may be difficult to provide or may be restricted, unless provided by the actual patient. Furthermore, existing estimation resources may be limited to by available information or restricted to a particular nearby location and thus may not reveal a desirable service provider in a neighboring location or sort results according to cost, reputation, acceptable insurances or other specific details.

Embodiments of the present disclosure implement systems, methods and tools for sharing medical costs between prospective patients (participants seeking treatment) and existing patients (medical data providers) participating as part of the medical network. As part of the medical cost sharing program, prospective patients may actively query medical costs and EOBs for specific conditions and treatments for the specific conditions previously experienced by existing patients. The existing patients participating and contributing to the documents accessible by the medical network may upload redacted versions of EOBs, medical bills and other medical documents to the medical network in exchange for points and rewards.

In some embodiments of the system, methods and tools for sharing medical costs, a prospective patient may access the medical network via an interface accessible through a network portal. For instance, an internet accessible web portal hosted by a web server accessed by a thin client such as a web browser. The prospective patient may log into a user account via the website or login page and query existing treatment costs and documents stored by the medical network. The prospective patient may communicate and query the desired information using natural language inputs, by talking through a microphone or using voice commands to instruct a client computing system to search the medical network for relevant treatment information. The prospective patient may use natural language commands or other inputs to filter the query results by condition, location, cost, quality of service, service provider, insurance provider, or any other parameter that may be detailed by the medical documents accessible through the medical network.

In some embodiments, the search results may be analyzed by a computing system, prioritized and presented to the prospective patient based on the relevancy of the search result to the search criteria inputted by the prospective patient during the natural language input command. The Prioritized search results may include relevant patient information such as age, condition, quality of service, cost of the service, location relative to the prospective patient, the doctor providing the service, insurance company and the coverage of the services paid for by the insurance company. As part of the analysis performed, each of the results may be attributed an overall score based on the relevancy to the search criteria provided by the prospective patient. The overall score may be attributed by one or more systems making up the medical network, analyzing the search criteria and queried results using data analytics to assess the best balance of cost, service, location, cost, etc. in order to predict the most desirable and accurate service provider estimate for the prospective patient.

In some embodiments of the systems, methods and tools for sharing medical costs in a medical network, the prospective patient may access redacted medical records that may be uploaded by existing patients in order to determine an estimated cost for treatment from start to completion of the medical treatment. A prospective patient may access one or more of the uploaded redacted medical records and/or view a timeline of medical treatments comprising one or more medical bills, EOBs or other medical documents. A prospective patient may, from the prospective patient's client device, load and display each of the medical bills or EOBs returned by the prospective patient's query of the medical network's database of existing patients' medical documents. For example, the prospective patient may view a series of redacted EOBs uploaded by an existing patient receiving service near the prospective patient location. The medical documents relating to treatment of an existing patient's condition may be presented in a timeline, wherein the prospective patient viewing the timeline returned by the search query and select one or more EOBs to view more specific details of one or more particular documents of the timeline.

In some embodiments, existing patients accessing the medical network may separately login to a user profile having access to the medical network. The existing patients may choose to upload the existing patient's medical documents, including medical billings and EOBs. An existing patient logged into the medical network from a client computing system may administer a natural language input into a microphone or other voice receiving hardware and request to upload a document to the medical network. The existing patient may scan or digitize the medical document being uploaded. For example, the existing patient may use scanning hardware or a camera system connected to the existing patient's client computer system in order to create a digital copy of a paper document. Alternatively, if the medical document is already in a computer readable format, the existing patent may transmit the computer readable copy of the medical document being submitted to the medical network.

Once uploaded to the medical network, the image of the existing patient's document may be converted to machine encoded text. For instance a computer system receiving the uploaded document may implement optical character recognition (OCR) software on the documents to convert the images of text to machine encoded text that may be understood by the computer systems of the medical network. The different fields of the uploaded document may be further analyzed and tagged by the computer systems or client devices of the medical network. For instance, the uploaded documents may be tagged with identifiers for the fields of date, location, cost, wait time, service provider, patient age and insurance provider and the service provided.

Existing patients may further issue additional commands via natural language command inputs to redact portions of the uploaded documents. In particular, an existing patient may redact private information that could be used to identify the particular existing patient. For example, the existing patient may execute a natural language command to redact information on the tagged document, including the patient's name, address, phone number, social security number, credit card/payment information, insurance claim id numbers, patient id numbers, or any other additional information that may be considered private or improper for other individuals to access.

System for Sharing Medical Costs

Referring to the drawings, FIGS. 1-9 illustrate a diagram of an embodiment of a system 100 for sharing medical costs throughout a medical network 150 of computer systems, consistent with the disclosures of this application. Embodiments of system 100 may comprise specialized computer systems 101a, 101b, 101c, 101d (collectively referred to as "client devices 101"), 110 connected together through network 150. Client devices 101 may include computer systems such as smartphones, tablets, desktop computers, laptops, etc., accessing the medical network 150 using wired or wireless network communications. The specialized computer systems 110 forming the network 150 may be referred to as nodes 110 and may comprise system hardware 160 or virtualized hardware 170 as exemplified in the drawing of FIG. 2. For example, computer systems forming the hardware backbone of the medical network 150 may include mainframes 161, RISC architecture based servers 162, servers 163, blade servers 164, storage devices 165 and networking components 166. The specialized computer systems 101, 110 of the medical network 150 may have a specialized configuration of hardware, software or a combination thereof as depicted in FIGS. 1-9 as network application server software 167, database software 168, medical network module 303 and as described throughout the present disclosure. Embodiments of the computer systems 101, 110 may comprise one or more elements of the generic computer system 1100 of FIG. 11, described in detail below. The elements of the generic computer system 1100 may be integrated into each of the specialized computer systems 101, 110 described herein.

Embodiments of the computer systems 101, 110 operating as specialized computer systems may include a processor 317, 1191, specialized hardware or circuitry, chipsets and/or software loaded in the memory device 316, 1194, 1195 of the computer system 101, 110. Each of the computer systems 101, 110 connected to the medical network 150 may perform one or more functions, tasks or routines relating to creating, searching, storing, uploading, analyzing and accessing medical documents and EOBs available through the medical network and interface thereof.

Embodiments of the specialized hardware and/or software integrated into the computer systems 101, 110 of the medical network 150 may be integrated into the computer systems 101, 110 as part of the medical network module 303, 331, 341. The medical network modules 303, 331, 341 may include hardware components and software applications performing each of the functions of the computer system 101, 110 including, but not limited to the creating, searching, storing, uploading, analyzing and accessing medical documents and EOBs available through the medical network 150. As used herein, the term "module" may refer to a hardware module, software-based module or a module may be a combination of hardware and software resources of the computer systems 101, 110 and/or resources remotely accessible to the computer system 101, 110 via the medical network 150.

The hardware and/or software components of the computer systems 101, 110 of the medical network 150 may each include one or more sub modules performing one or more specific tasks of the computer systems 101, 110 sharing medical costs between one another over the medical network 150. The sub modules actively performing the tasks of a particular computer system 101, 110 may vary depending on the function of the computer system 101, 110 while accessing the network 150. For example, in some embodiments, a computer system 110 of the network 150 may be an analytics processing system 301 having a medical network module 303 actively engaging in the use of one or more sub modules such as a character recognition module 307, cognitive processing module 309, notification engine 310, AI natural language processor 311, scoring engine 313, reporting engine 314 and a rewards engine 315.

Likewise, a client computer system 101 connected to the medical network 150 may be a prospective patient client device 330 and/or an existing patient client device 340. A "prospective patient" may refer to a person or user accessing that medical network 150 for the purpose of estimating medical costs. An "existing patient" may refer to a person or user accessing the medical network 150 to upload or provide medical documents such as billings or EOBs to the medical network 150. A client device 101 that is operating as a prospective patient client device 330 may comprise a medical network module 330 having active sub modules of a guided search module 333 and a results drill down module 335. A client device 101 operating as an existing patient client device 340 may include as sub modules of the medical network module 341, an upload module 343 and a context augmentation interface module 345.

Embodiments of system 100, may include a plurality of computer systems 101, 110 connected and placed in communication with one another over a computer network 150, including one or more computing nodes 110 and client devices 101. Embodiments of the network 150 may be constructed using wired or wireless connections between each hardware component connected to the network 150. As shown in the embodiment of a cloud computing network 100 of FIG. 1, each of the computer systems 101, 110 may connect to the network 150 and communicate over the network 150, for example using a network interface controller (NIC) 319 or other network communication device. Embodiments of the NIC 319 may implement specialized electronic circuitry allowing for communication using a specific physical layer and a data link layer standard, such as Ethernet, Fiber channel, Wi-Fi or Token Ring. The NIC 319 may further allow for a full network protocol stack, enabling communication over network 150 to the group of computer systems 101, 110 or other computing hardware devices linked together through communication channels.

The network 150 may facilitate communication and resource sharing among the computer systems 101, 110 and additional hardware devices connected to the network 150. An example of the medical network 150 may include cloud computing networks 100, however it should be understood that although this disclosure includes a detailed description of a cloud computing network 150, implementation of the teachings recited herein are not limited to a cloud computing environment. Rather, embodiments of the present disclosure are capable of being implemented in conjunction with any other type of computing environment now known or later developed. For instance, the medical network 150 may include a local area network (LAN), home area network (HAN), wide area network (WAN), back bone networks (BBN), peer to peer networks (P2P), campus networks, enterprise networks, the Internet, and any other network known by a person skilled in the art.

Cloud computing is a model of service delivery enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models. The characteristics of the cloud computing model may be described as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

The service models under a cloud computing environment may be described as follows:

Software as a Service (SaaS): the capability provided to the consumer is to use the provider's applications running on a cloud infrastructure. The applications are accessible from various client devices 101, 330, 340 through a thin client interface 405 such as a web browser 403 (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

The deployment models of cloud computing environments may be described as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment may be service oriented with a focus on statelessness, low coupling, modularity, and semantic interoperability. At the heart of cloud computing is an infrastructure that includes a network of interconnected nodes 110.

Referring to the drawings, FIG. 1 is illustrative of a medical network 150 operating as a cloud computing environment. As shown, the cloud computing environment may include one or more cloud computing nodes 110 with which client computing devices 101 used by cloud consumers, such as, for example, desktop computers 101a, 101d, laptop computers 101b, and digital assistant (PDA), tablet computers or cellular telephone 101c may communicate. Computer system nodes 110 may communicate with one another and may be grouped (not shown) physically or virtually, in one or more networks, such as Private, Community, Public, or Hybrid clouds as described hereinabove, or a combination thereof, allowing for the cloud computing environment of the medical network 150 to offer infrastructure, platforms and/or software as services for which a cloud consumer does not need to maintain resources on a local computing device 101. It is understood that the types of computing devices 101 shown in FIG. 1 are intended to be illustrative only and that nodes 110 and cloud computing environment can communicate with any type of computerized device over any type of network and/or network addressable connection (e.g., using a web browser).

Figure 2:
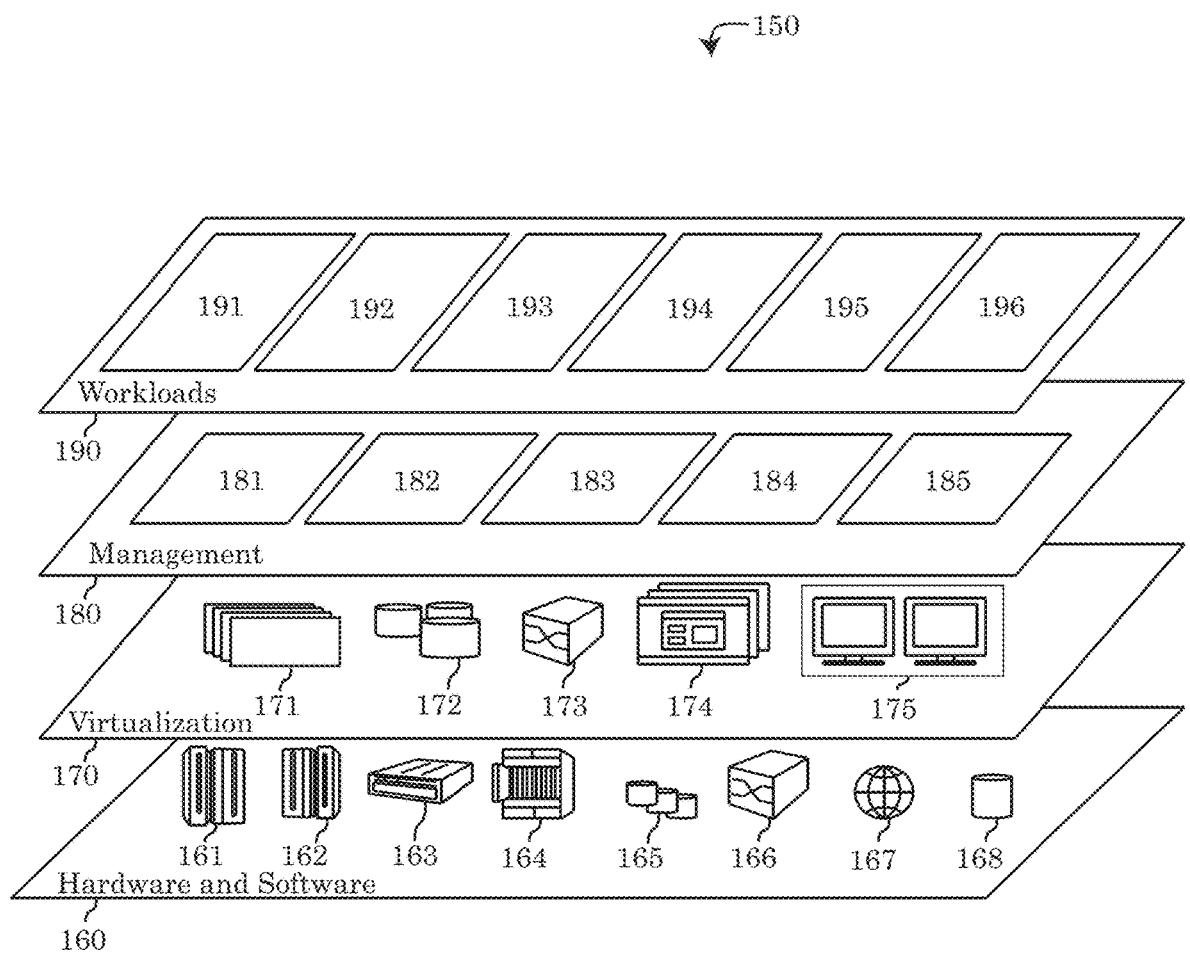
FIG. 2 illustrates abstraction model layers of a cloud computing environment consistent with the embodiments of the present disclosure.

Referring now to FIG. 2, a set of functional abstraction layers provided by a cloud computing environment of the medical network 150 is shown. It should be understood in advance that the components, layers, and functions shown in FIG. 2 are intended to be illustrative only and embodiments of the invention are not limited thereto. As depicted, the following layers and corresponding functions are provided:

Hardware and software layer 160 includes hardware and software components. Examples of hardware components include: mainframes 161; RISC (Reduced Instruction Set Computer) architecture based servers 162; servers 163; blade servers 164; storage devices 165; and networking components 166. In some embodiments, software components may include network application server software 167 and database software 168.

Virtualization layer 170 provides an abstraction layer from which the following examples of virtual entities may be provided: virtual servers 171; virtual storage 172; virtual networks 173, including virtual private networks; virtual applications and operating systems 174; and virtual clients 175.

Embodiments of the management layer 180 may provide the functions described below. Resource provisioning 181 provides dynamic procurement of computing resources and other resources that are utilized to perform tasks within the cloud computing environment. Metering and Pricing 182 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 183 provides access to the cloud computing environment of the medical network 150 for consumers (i.e. prospective and existing patients) and system administrators. Service level management 184 provides cloud computing resource allocation and management such that required service levels are met. Service Level Agreement (SLA) planning and fulfillment 185 provides pre-arrangement for, and procurement of, cloud computing resources for which a future requirement is anticipated in accordance with an SLA.

Workloads layer 190 provides examples of functionality for which the cloud computing environment may be utilized. Examples of workloads and functions which may be provided from this layer include: records management 191; web page management 192; searching and results management 193; data analytics processing 194; profile management 195; and natural language processing 196 of natural language input commands.

Figure 3:
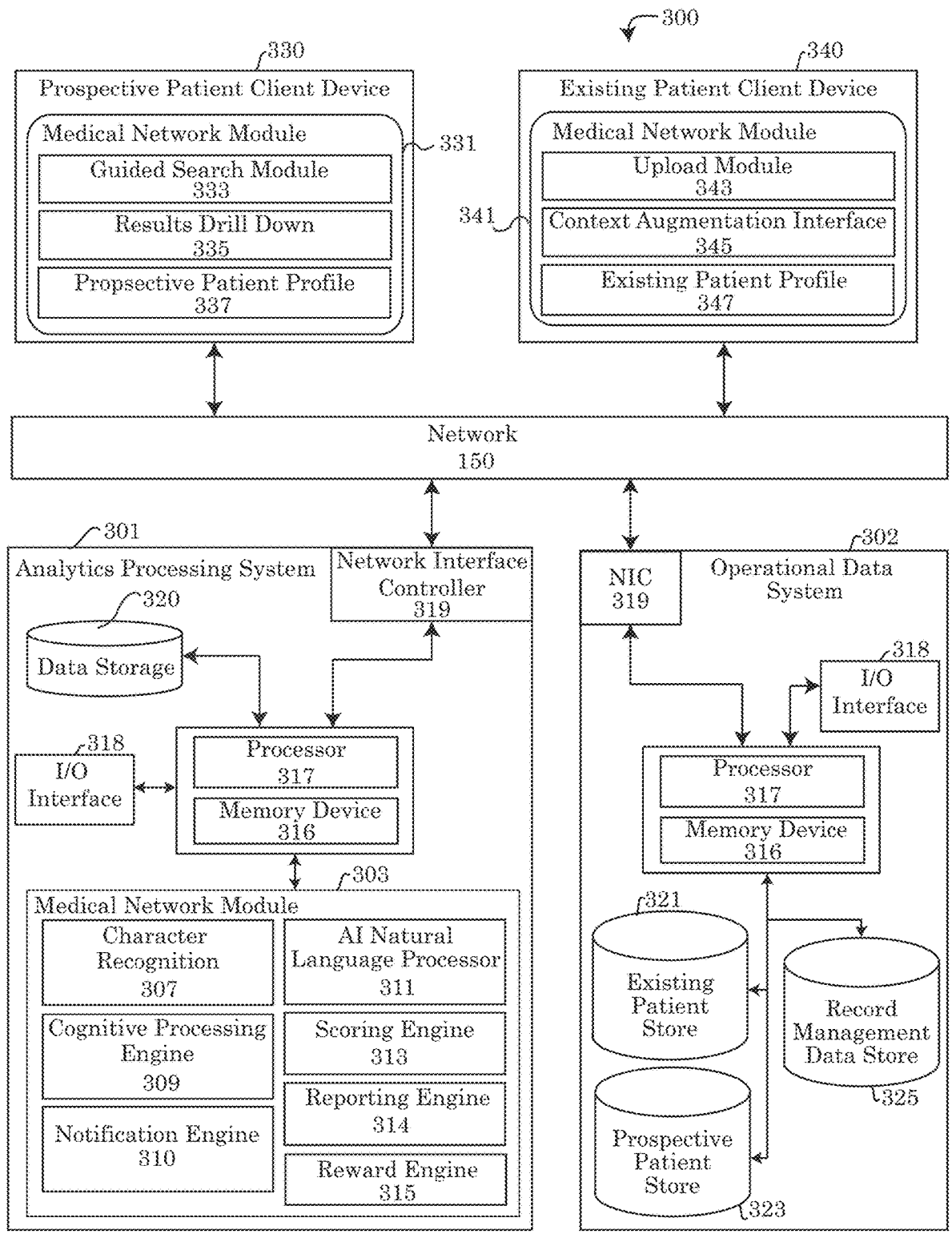
FIG. 3 depicts a block diagram of an embodiment of a system for sharing medical costs to a medical network.

Referring to the drawings, FIG. 3 illustrates a diagram of an embodiment 300 of system 100 for sharing medical costs participating members of a medical network 150. Embodiments of system 300 may comprise a plurality of medical network 150 nodes 110 and client devices 101. For instance, as shown in FIG. 3, the system 300 may include an analytics processing system 301 and an operational data system 302, each acting as a node 110 of the medical network 150, whereas the prospective patient client device 330 and existing patient client device 340 may each act as separate and/or independent client devices 101 connecting to the medical network 150 for the purpose of estimating medical costs or providing documents to the medical network 150 allowing for prospective patients to estimate medical costs.

Embodiments of the analytics processing system 301 may be a computing system comprising hardware and software components as depicted in embodiment 300 and in some embodiments, may integrate one or more components of a generic computer system 1100 described in detail below. Embodiments of the analytics processing system 301 may comprise a processor 317, memory device 316, an input/output (I/O) interface 318 and one or more computer readable data storage devices 320 as understood by individuals skilled in the art and in accordance with processors, memory devices, I/O interfaces and computer readable storage devices that may be part of a generic computing system 1100. Embodiments of the Analytics processing system 301 may include a medical network module 303 comprising specific hardware modules, software modules loaded into the memory device 316 and a combination of hardware and software.

Embodiments of the medical network module 303 may include a character recognition module 307. The character recognition module 307 may perform the function or task of recognizing printed or written text characters on images of medical documents uploaded to the medical network 150 by client devices 101, 340. Embodiments of the character recognition module may apply optical character recognition (OCR) to medical documents such as EOBs and billings provided to the medical network 150. The character recognition module 307 may perform the function of photo scanning each character of text, character-by-character, analyze the image of the uploaded document and translate the character images into machine-encoded text, such as ASCII.

In some embodiments of OCR processing the scanned-in image or bitmap may be analyzed by the character recognition module 307 for light and dark areas in order to identify each alphabetic character or numeric digit inputted into the medical document. When the character recognition module recognizes a character in an uploaded document, the character may be converted into an ASCII code. In some embodiments, the character recognition module 307 may comprise specialized circuit boards and chips that may be designed expressly for OCR which may speed up the recognition process.

Embodiments of the medical network module 303 of the analytics processing system 301 may also comprise a cognitive processing engine 309. The cognitive processing engine 309 may perform the task of enabling prospective patients, and existing patients accessing the medical network 150, to interact with the medical network 150 as a dialog driven interface 403. For example, FIGS. 4-9 depict an embodiment of a dialog driven interface 405 accessed via thin client 403. The interface 405 may be displayed on a display device 401 of the patient's client device 330, 340. The dialog driven interface 403 may present system generated dialogue 410*a*, 410*b* (referred to generally hereinafter as "system generated dialogue 410"). As part of the dialogue driven interface 403, a patient accessing the medical network 150 may receive system generated dialogue 410 prompting a response from the patient using a natural language input command 407*a*, 407*b* (referred to hereinafter generally as "natural language input command 407"). In some embodiments, a patient may respond to the system generated dialogue 410 by inputting natural language inputs into a microphone or voice input system. In alternative embodiments, a patient may interact with the system generated dialogue 410 by inputting written responses via a keyboard, virtual keyboard, touch screen or other input device that may be connected to an I/O interface of the client device 330, 340.

The cognitive processing engine 309 may operate as a simulation of the human thought process in a computerized model. Embodiments of the cognitive processing engine 309 may involve self-learning systems that may use data mining, pattern recognition and natural language processing to mimic the way a human brain functions, draws conclusions and inferences. The cognitive processing engine 309 may be capable of acting as an automated system for solving problems and generating responses without human assistance.

Embodiments of the cognitive processing engine 309 may form ontologies to formally name, organize and define the properties of the data being received by the cognitive processing engine. For example, common components of an ontology formed by the cognitive processing engine 309 may include individual objects, classes of objects, object attributes, relations between individual or classes of objects, function terms, restrictions, rules, axioms and events that may change attributes or relations.

One example of a cognitive processing engine 309 may be IBM's Watson computer system. Embodiments of the cognitive engine 309 may use machine learning algorithms in order to continually acquire knowledge from the data fed to the cognitive processing engine 309 which may be from mining data information and interacting with patients through the dialog driven interface 405. From the data provided to the cognitive processing engine 309 and the natural language input commands 407, the cognitive processing engine 309 may be able to derive the context of back and forth dialogue between the patient and the analytics processing system 301. For example, a natural language input that includes the phrase "torn ACL" may be identified with the context of the patient suffering an injury. The context may further provide the cognitive processing engine 309 with a particular set of requirements for performing a query of similar cases for which the analytics processing system may compare (i.e. searching for torn ACL cases as a requirement of the search).

In some embodiments of the analytics processing system 301, the cognitive processing engine may further perform a sentiment analysis of the natural language input commands to more accurately derive contextual clues about the information being received from a patient. Sentiment analysis may refer to analyzing natural language, text, computational linguistics and biometrics in order to systematically identify, extract, quantify and study the affective state of the subjective information being provided by the patient during the back and forth dialogs 407, 410 using the interface 405. The sentiment analysis can determine the attitude or emotions of the patient or other user inputting the natural language or text into the interface 405. Using the sentiment analysis, the cognitive processing engine 309 may classify the polarity of the speech or text provided by the patient and determines whether the language provided is positive, negative or neutral and whether there is an associated emotional state that may be derived, such as angry, sad, happy, etc.

Embodiments of the cognitive processing engine 309 may operate alongside the AI natural language processor 311 (referred to herein as "NLP 311"). The NLP 311 may perform the function of analyzing, understanding and generating languages that the patients or users of the dialog driven interface 405 may use natural language to interact with the analytics processing system 301 of the medical network 150. The NLP 311 may teach the analytics processing system 301 to understand human speech and language and thus formulate responses to the inputs provided by patients in return.

In some embodiments, the NLP 311 may be programmed to understand context and linguistic structures of human speech in order to better understand the natural language input commands 407 provided to the analytics processing system 301. The NLP 311 receiving natural language input commands 407 may analyze the text of the input command 407, and break the unstructured text into situational criteria, preferences of the patient, location details and other contextual details. The NLP 311 may use machine learning or other artificial intelligence techniques to examine and analyze patterns in the speech or written data provided by the patients or data stored by the devices of the medical network 150 in order to improve the NLP's 311 programming. Tasks that may be performed by the NLP 311 may include sentence segmentation, part-of-speech tagging, parsing of the speech inputs provided to the NLP 311, deep analytics of data sets and named entity extraction.

Figure 4:
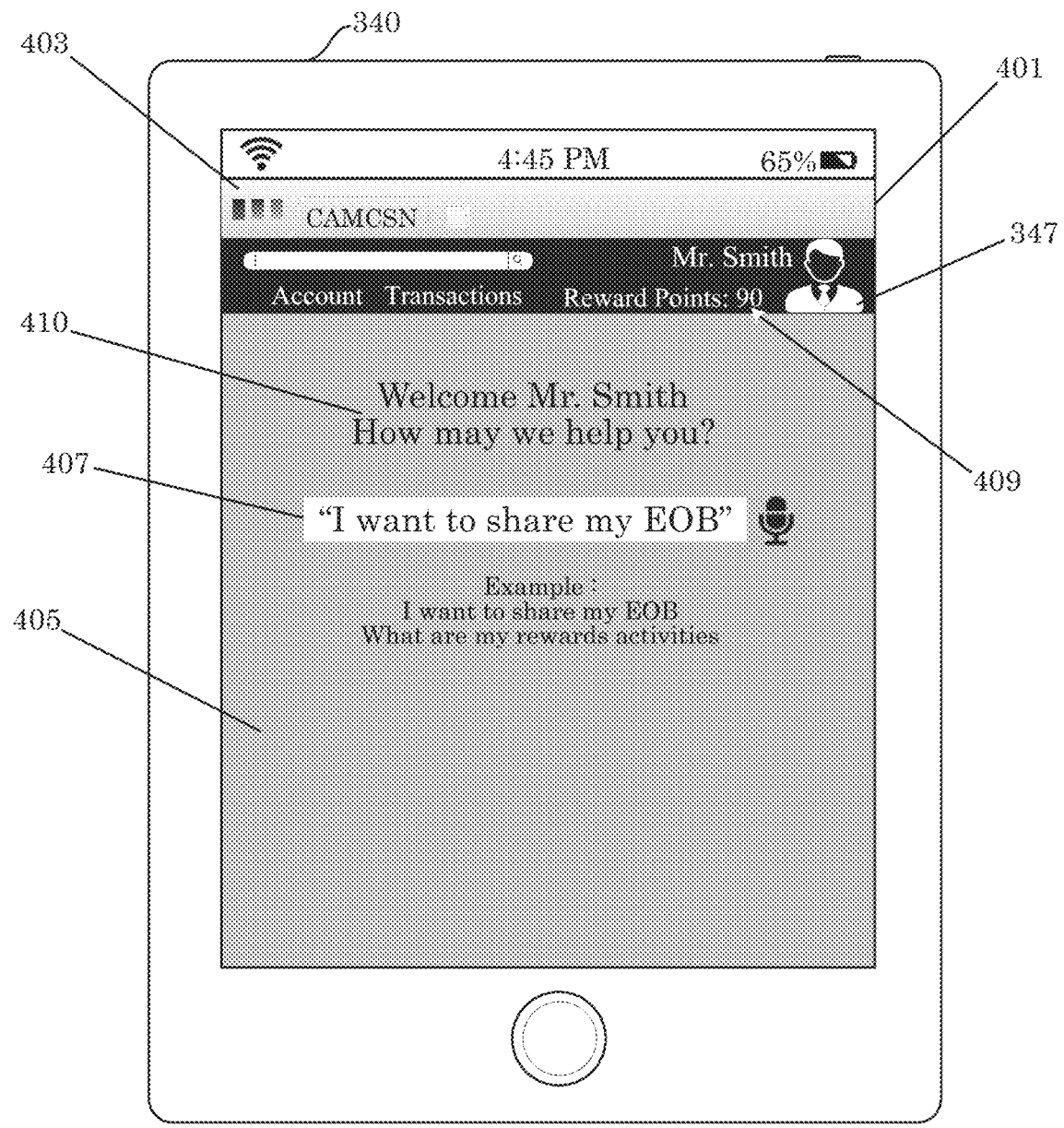
FIG. 4 illustrates an embodiment of an interface of a medical network inputting a natural language command to share medical documents.
Figure 6:
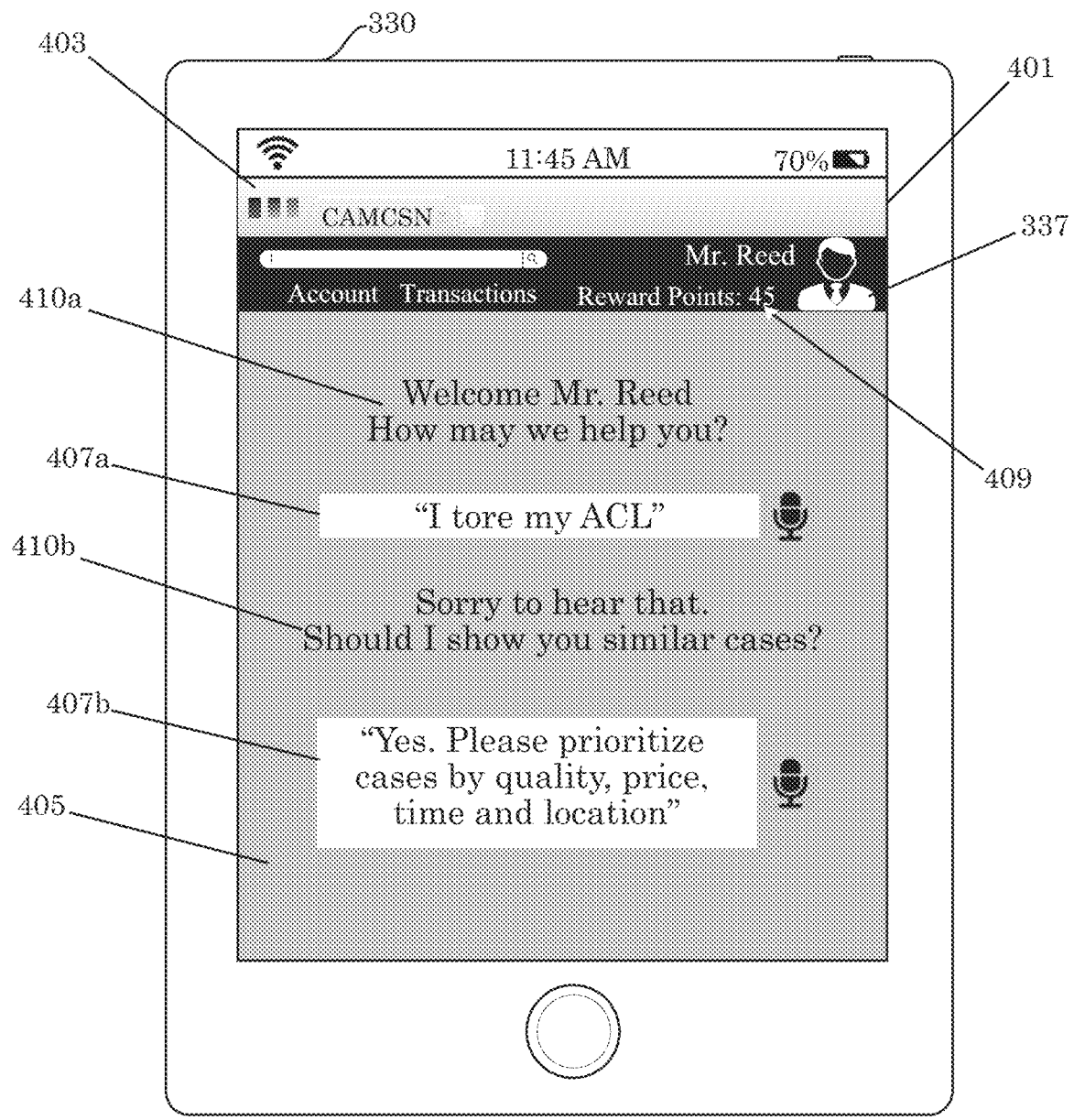
FIG. 6 illustrates an embodiment of an interface of a medical network inputting a natural language command to search similar cases to the user.
Figure 7:
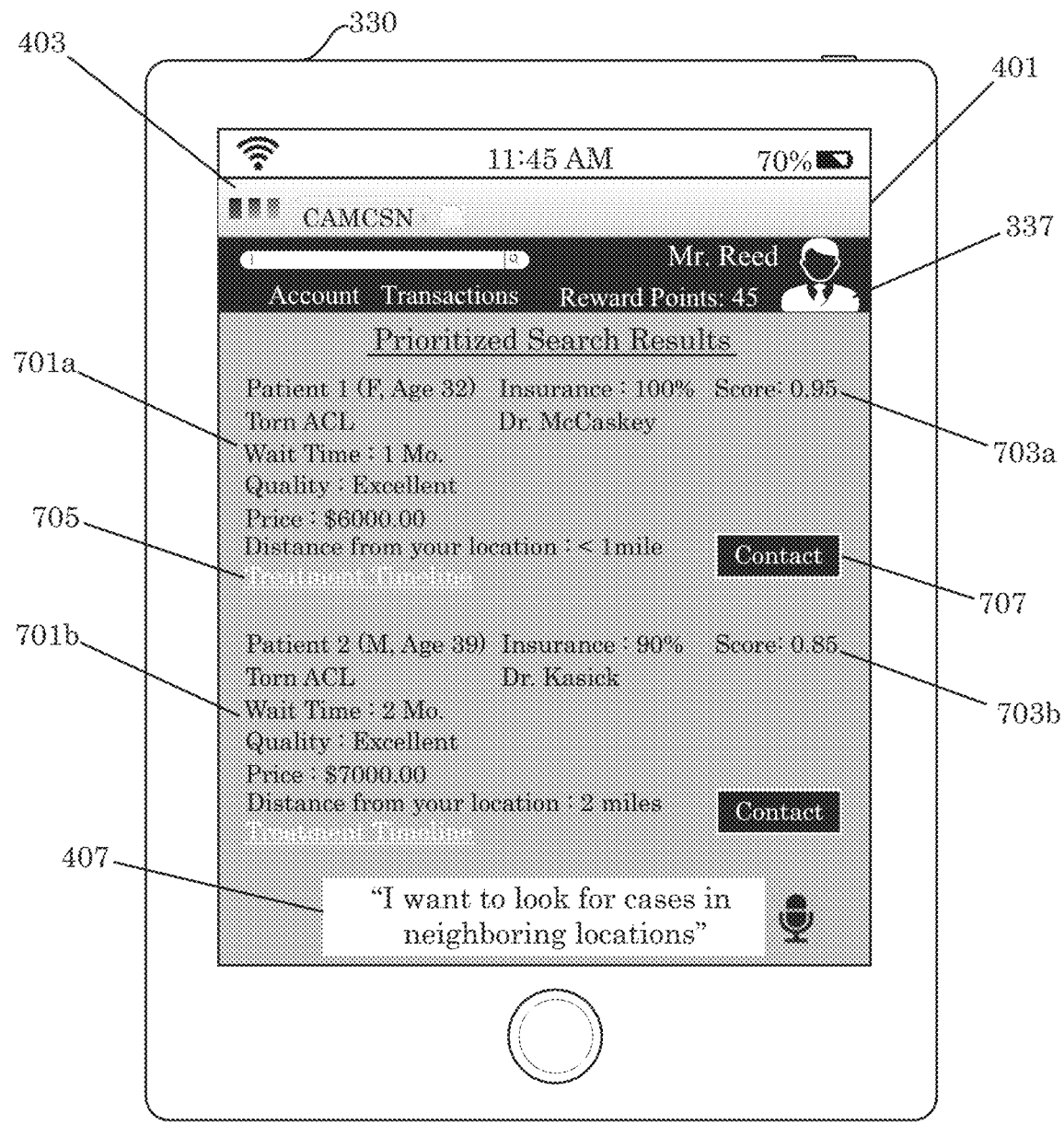
FIG. 7 illustrates an embodiment of an interface of a medical network displaying prioritized search results of similar medical cases.

The NLP 311 may receive natural language input commands 407 or written commands spoken by a patient or user and respond using human language of the input rather than programming code. For example, as shown in FIGS. 4 and 6, the analytics processing system 301 may present system generated dialog 410 in a human language such as English, receive a response from a patient in the patient's natural language, process the context of the patient's message and respond accordingly. For instance, as shown in FIG. 6, the analytics processing system 301 may display on the interface 405 a welcoming message asking how the medical network 150 may help the patient. The patient may provide a natural language input command 407*a*, which may describe the patient's current condition, in this example, "I tore my ACL". As shown in the example, the NLP 311 understands the condition described by the patient and suggests showing the patient similar torn ACL cases for the purpose of estimating medical costs (as shown in FIG. 7). The NCL 311 may understand different prioritization and results filtering requests made by a patient. As shown in FIG. 6, a patient provides a natural language input command 407*b* requesting the system 301 to prioritize the torn ACL cases by quality, price, time and location. The NLP 311 receives the proposed natural language command 407*b* and presents the results shown in FIG. 7 by prioritizing the torn ACL cases using the parameters requested by the patient.

In some embodiments of the system 300, the medical network module 303 of the analytics processing system 301 may comprise a notification engine 310. The notification engine 310 may perform the task and/or function of delivering messages to patients and participants of the system 300. The notification engine 310 may send communications relating to the activity of a particular patient or a participant's account. A patient or participant of the medical network may set preferences of the notification engine 310 within the patient's profile 337, 347 which may grant permission or identify the types of notifications that may be considered acceptable for transmission. Communications may be transmitted to the patient or patient's client device 330, 340 via email, short messaging service (SMS), push notifications or via a direct messaging service.

The notification engine 310 may alert or message a patient about the availability or status of another patient or user accessing the medical network in some embodiments. In other embodiments, the notification engine 310 may alert a patient's client device 330, 340 if the client device 330, 340 is receiving a contact request from another patient or user. The notification engine 310 may also transmit notifications to an existing patient's client device 340 informing the existing patient that one or more medical documents uploaded by the existing patient has been returned in a query performed by a prospective patient's client device 330 and/or selected by a prospective patient during a query performed by a perspective patient accessing the medical network 150. In some embodiments, the notification engine 310 may further alert a particular patient or user that a report generated by the reporting engine 314 has been created or received.

In some embodiments of the analytics processing system 301, the system 301 may include a scoring engine 313. The scoring engine 313 may perform the function of analyzing the search results returned from the prospective patient's query of the operational data system 302, the existing patient store 321 and the record management store 325, analyze each of the fields within the tagged medical documents returned by the query and compare the value of the fields with the search criteria in order to generate a relevancy score 703a, 703b (referred hereinafter generally as "relevancy score 703"). The scoring engine may rate each of the evaluated medical documents returned from the query based on the criteria of the search including the condition treated, the cost of treatment, the patient's age, insurance carrier, quality of service, and distance between the location of the prospective patient and the service provider. The more closely each of the criteria of the search match the values of the fields entered into the medical records returned by the query, the higher the relevancy score 703 assigned to the particular medical document may be. The analytics processing system 301 may prioritize the search results of the query by relevancy score 703 and display to the prospective patient a prioritized list of the search results, wherein the search results are organized by relevancy score.

Using the illustrative example of FIG. 7, each of the medical documents 701a, 701b of the query may have different amounts of criteria matching the particular search criteria designated by the prospective patient and/or provided by the prospective patient's profile 337. By leveraging the cognitive processing engine 309, the scoring engine 313 may use the conclusions and inferences of the cognitive processing engine 309 to assign a score 703 to each search result, wherein the closer the search criteria from the prospective patient is to the information provided in each entry 701a, 701b, the higher the relevancy score 703 that may be assigned to the entry 701a, 701b. As seen in the example of FIG. 7, the first entry 701a belonging to Patient 1 may be assigned a relevancy score 703a of 0.95 whereas the second entry 701b may be assigned a lower relevancy score 703b of 0.85. Conclusions may be drawn that the first entry 701a is a more relevant or desirable estimation of the medical costs incurred for the conditions searched by the prospective patient.

In this example, the relevancy scores 703 of each entry 701a, 701b may vary depending on the search criteria and prospective patient. While both entries are for treatments of a torn ACL, the cognitive processing engine 309 and the scoring engine 313 may determine which entry 701a, 701b may be the most relevant. In this case, the possible reasons that may be considered a better match between the prospective patient and Patient 1 of the first entry 701a, may be attributed to the lower overall costs between the entries ($6000 vs $7000), the lower wait time experienced by Patient 1 using the particular service provider (1 mo. vs 2 mo.), the close proximity of the service provider in the first entry 701a (<1 mi. vs. 2 miles) to the prospective patient and the percentage of insurance coverage experienced by the patient of each entry (100% vs. 90%). When each of the variables of the entries 701 are analyzed and taken into account, it can be see for the particular torn ACL example, the scoring engine may identify the first entry 701a as a closer representation of expected costs, a better deal, better quality, etc. and thus the scoring engine may assign a higher relevancy score 703 to the first entry 701a over the second entry 701b. It should be noted that the simplicity of the example in FIG. 7 is for illustrative purposes only. An actual search query performed by a perspective patient may yield much more than two results in some instances. The number of results may only be limited by the total number of entries stored by the system 300.

In some embodiments, a prospective patient may choose to weight specific characteristics of the search as more important to the patient and thus the weighting of a particular field in each entry may affect the prioritization of the search results returned by the scoring engine 313 to the prospective patient's client device 330. For example, a prospective patient may identify the quality of service, service location and costs as being greater factors for prioritization of the search results. Accordingly, the scoring engine 313 in coordination with the cognitive processing engine 309 may score each search result of the query with a higher focus on the weighted fields selected by the prospective patient conducting the query. In another instance, a prospective patient may deem that costs and insurance coverage may be the most important factors, thus skewing the relevancy scores of the results toward medical documents where the service provider treated the condition more cheaply and through the use of insurance.

The analytics processing system 301 in some embodiments may further comprise a reporting engine 314. The reporting engine 314 may include tools or software applications capable of extracting the data of the queries and prepare one or more reports based on the queries received by the analytics processing system. For example, the reporting engine 314 may be a dashboard accessible by a user, patient or administrator of the system 300. Embodiments of the reporting engine 314 may be responsible for returning the prioritized search results generated by a query performed by a perspective patient. The reporting engine 314 may also provide detailed statistics, log events of each query and generate reports about the overall use of the medical network 150 by each of the users, patients and system administrators.

In some embodiments, the reporting engine 314 may access the data stored by the operational data system 302 to generate one or more reports. The reporting engine 314 may analyze the data transmitted, received and stored by the operational data system 302, including data stored by the existing patient store 321, prospective patient store 321 and the record management store 325. Based on the data of the operational data system 302 analyzed by the reporting engine 314, the reporting engine 314 may create one or more reports describing the trends of the system 300. The trends described in the report may include those trends relating to the requirements of each query and the matching results generated by the reporting engine 314. For example, individual users may be able to generate a report depicting the number of times other participants of the medical network have accessed a particular set of profile information, a specific set of medical documents, existing patients that have uploaded the most medical documents, prospective patients that have made the most queries and the number of times the medical network has facilitated contact between prospective and existing patients.

The reporting engine 314 may also identify and report the total number of searching being performed by users of the medical network 150, the overall availability of EOBs by location, statistics about the costs of treatment of each particular condition as a function of location, the relative quality of treatment based on locations and the types of services available by location. Users and patients of the system 300 may access and request these reports in order to receive and display the reports on a display device, such as the display device 401 of the prospective patient client device 330 or the existing patient client device 340.

Embodiments of the system 300 may further include a reward engine 315. The reward engine 315 may perform the task of tracking, monitoring, updating, distributing and allocating incentives provided to existing patients and other participants of the network 150 for uploading medical documents to the medical network 150. Rewards 409 may be in the form of points, perks, coupons, discounts, gifts, rebates etc. In the exemplary embodiment presented in FIGS. 4-9, the rewards 409 are shown in the form of points, which may be used as a form of currency on the medical network 150 for purchasing goods and services or may be used as currency to access medical documents stored by the operational data system 302. For example, conducting searches of the operational data system 302, viewing the results or viewing detailed EOBs may cost a specific number of points to access in some embodiments. Participants of the network 150 may thus upload their own medical documents in exchange for points to trade in for accessing the medical documents uploaded to the network 150 by other participants.

The reward engine 315 may allocate points or other rewards 409 to existing patients that upload medical documents to the medical network 150 or whom participate in providing useful information to the medical network 150. Useful information may include feedback and ratings about service providers and/or other patients (i.e. if the participant is a service provider). The reward engine 315 may monitor the operational data system 302 for the occurrence of transactions, such as feedback or uploaded medical documents. The transactions may each be tagged with a user profile that participated in the transaction. The rewards engine 315 may be search a set of programmable rules to determine which transactions should result in the allocation or deduction of points or other rewards and apply the allocation or deduction to the reward values of the profiles participating in the transaction. Moreover, in some embodiments, of the system 300, the rewards engine 314 may save or store records and the history of each transaction for auditing and reporting purposes. In some instances, participants receiving or spending rewards 409 may access the transaction records stored by the rewards engine 314.

Embodiments of the system 300 may further comprise an operation data store 302. The operational data store may be a specialized computer system and/or node 110 of the medical network 150 tasked with maintaining and serving the data stored by the medical network 150 which may be provided by existing patients or accessed by prospective patients. In some embodiments, the operational data store may be a separate node 110 or computer system from the analytics processing system 301. In alternative embodiments, the operational data store 302 may be integrated into the analytics processing system 301. For example, the analytics processing system 301 may include each of the data stores 321, 323, 325 as part of the data storage 320 accessible to the analytics processing system 301.

Embodiments of the operational data system 302 may store a plurality of different types of data and in some embodiments may organize the data into distinct data structures. Examples of the data structures may include an existing patient store 321, a prospective patient store 323 and a record management data store 325. In some embodiments, each participant of the medical network 150 may have a separate physical or virtual data store containing record information about each participant, whereas in alternative embodiments, groups a perspective and existing patients may have information stored collectively in the prospective patient data store 323 or existing patient data store 321 respectively.

Embodiments of the existing patient data store 321 may perform the function or task of storing links to stored documents uploaded and maintained by the record management data store which holds a copy of each medical document provided to the medical network 150. When a medical document is uploaded by an existing patient, a record of the uploaded document may be created in the existing patient data store 321. The record of the upload may include Meta data describing each of the fields of the uploaded document and further comprise a pointer directing the record of the uploaded document to the storage location of the uploaded document within the data structure of the record management data store 325.

Figure 9:
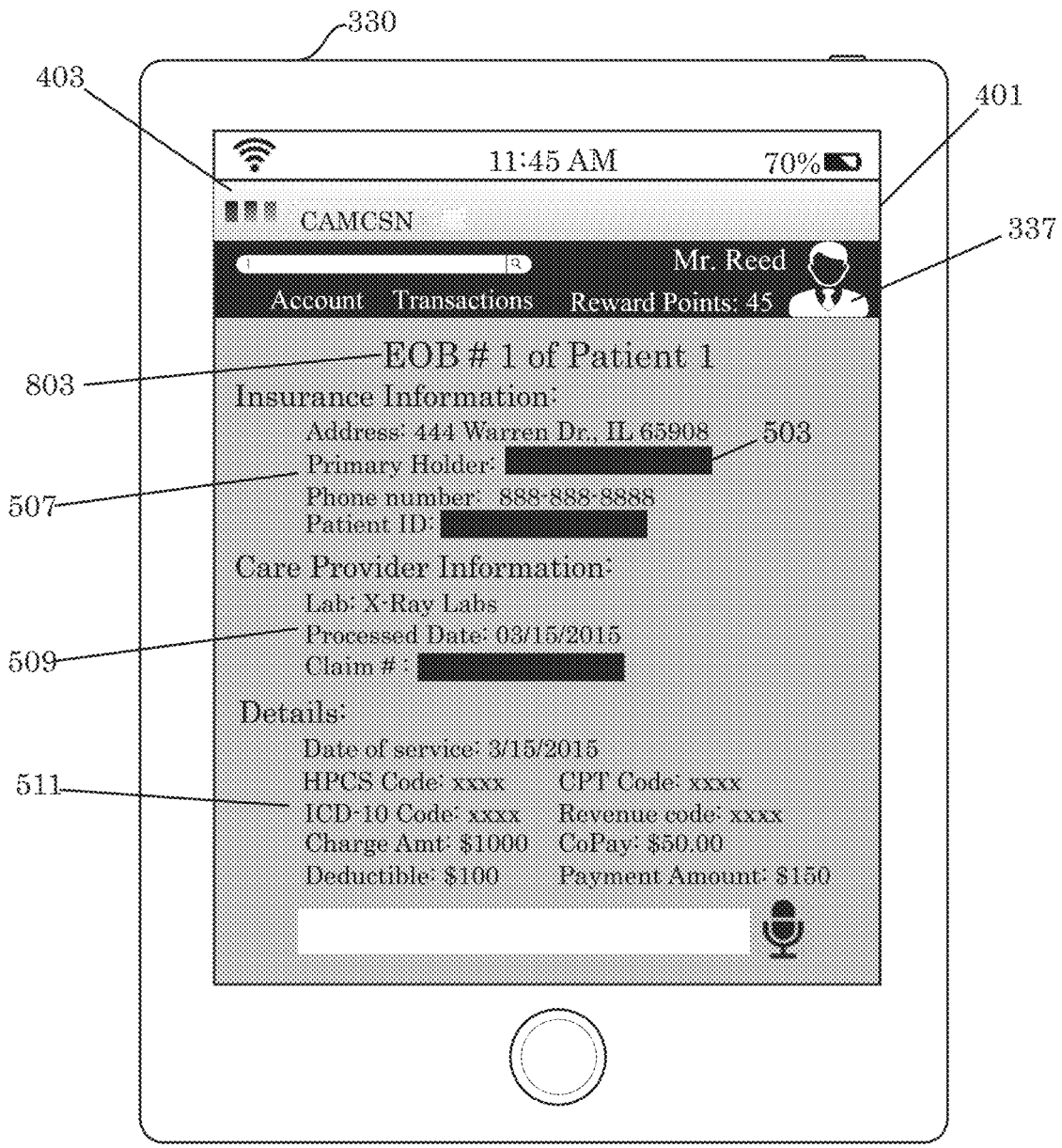
FIG. 9 illustrates an embodiment of an interface of a medical network displaying an explanation of benefits (EOB) document of one entry of the timeline of treatment of FIG. 8.

Embodiments of the existing patient data store 321 may further store specific user settings for each existing patient profile 347, including privacy settings. The privacy settings may include permissions to receive notifications, messages from other participating users of the medical network (such as prospective patients) and default settings for redacting uploaded medical documents provided to the medical network. For example, an existing patient may create a default setting to anonymize any uploaded medical documents by redacting the patient's name, address, phone number, claim ID numbers, insurance ID numbers as shown in FIG. 9. Embodiment of the existing patient data store 321 may also store contact information provided by the existing patient profile 347, reward status 409, preferences for receiving reports from the reporting engine 314, the frequency of reports received from the reporting engine 314 and any feedback or ratings provided by the existing patient about service providers or other participants of the medical network 150.

Similar to the existing patient data store 321, the prospective patient data store 323 may be a data structure capable of organizing, storing and maintaining data relating to the prospective patients accessing the data network 150 from one or more prospective patient client devices 330. The prospective patient data store 323 may collect and store records and transactions relating to the prospective patient's profile 337. For example, the prospective patient data store 323 may save records of each prospective patient's current and previous queries of the medical data network, including queries of the record management data store 325. The prospective patient data store may maintain a log or history of each query performed by a perspective patient and the prospective patient may retrieve a record of the prospective patient's previous queries. In some embodiments, the prospective patient data store 323 may store each prospective patient's notification preferences, including the types of notifications that may be sent to the prospective patient, email addresses, mobile phone numbers, social media contacts and direct messaging user names that may be granted permission to receive notifications from the medical network 150.

Embodiments of the prospective patient data store 323 may further include records of each prospective patient profile's 337 default query preferences. For example, a prospective patient may be able to set a default location to query medical services as well as a default cost tolerance and insurance policy. Moreover, in some embodiments, the prospective patient data store may further maintain default weightings between different fields and variables that the prospective patient may select in order to weight the prioritized search results and relevancy scores 703 returned by a query conducted by the prospective patient. Also, similar to the data stored by the existing patient data store 321, the prospective patient data store 323 may also maintain a record of each prospective patient's reward status, reporting preferences and any feedback or ratings that may have been provided by the prospective patient toward an existing patient or service provider.

Embodiments of the operational data system 302 integrated into the system 300 may include a record management data system 325. The record management data store 325 may perform the task or function of storing each medical document maintained by the medical network 150, including all of the EOBs, medical bills, medical records and other medical documents uploaded to the medical network 150 by existing patients. Entries of the medical documents maintained by the record management data store 325 may be formatted, organized and tagged, allowing for faster searching and retrieval of the records when queried by prospective patient client devices 330 or the analytics processing system 301. The entries of the record management data store 325 may be accessed, amended or updated as requested by either the nodes 110 or the client devices 101 of the network 150.

The entries of the record management data store 325, may, upon request by another node 110 or client device 101, be transmitted by the record management data store 325 to the requesting device or computer system, such as the analytics processing system 301 which may subject the records to analysis by the cognitive processing engine 309 and the scoring engine 314, for the purpose of matching the records to the search criteria, identifying the most relevant records and applying a relevancy score 703 to each of the records that are displayed as part of the prioritized search results.

In some instances, the data records being managed by the record management data store 325, may be retrieved by the analytics processing system 301 for the purpose of performing a historical analysis of the medical records available on the medical network 150 in order to generate one or more reports by the reporting engine 314. The analytics processing system 301 may input data from the fields of each record maintained by the record management data store 325 and identify patterns and statistics relating to the data of the records then generate the report as a function of the patterns and statistical analysis performed. Moreover, in addition to using the data stored by the record management data store 325 for the purpose of generating reports, the data may further be analyzed by the cognitive processing engine 309 and/or the AI natural language processor 311 for the purpose of using machine learning to further improve the accuracy and intelligence of both of the engines 309, 311.

Embodiments of the system 300 may include one or more client devices 101 connecting to the medical network 150 in order to participate and access the features of the medical network 150 as described herein. Embodiments of the client devices 101 may include one or more existing patient client devices 340 which may be operated by existing patients whom may contribute medical data to the record management system in the form of EOBs, medical records and billings. Additional client devices 101 connecting to the medical network 150 may also comprise one or more prospective patient client devices 330. The prospective patients may include users and participants of the medical network 150 that may be seeking to search for medical cost estimations and query the medical network in order to view the records stored by the record management data store 325. Although the prospective patient client device 330 and the existing patient client device 340 are represented in FIG. 3 as two separate computing systems, in some embodiments, the prospective patient client device 330 and the existing patient client device 340 may be the same computer system, wherein the computer system is capable of changing operating modes from a prospective patient to existing patient operating mode and vice versa.

Referring to the drawings, FIG. 3 depicts a block diagram of an embodiment of an existing patient client device 340. The existing patient client device 340 may be any computing system, such as the generic computer system 1100 described in detail below. In addition to the generic computing elements such as the processor 1191, memory devices 1194, 1195 input devices 1192 and output devices 1193, the existing patient client device 340 may comprise a medical network module 341. The medical network module 341 may be a hardware module or a software module comprising programming code loaded into a memory device of the existing patient client device 340. Embodiments of the medical network module 340 may include an upload module 343, context augmentation module 345 and an existing patient profile 347.

Embodiments of upload module of the medical network module 341 loaded onto the existing patient client device 340 may perform the task or function of transmitting preparing and transmitting each of the medical documents selected by the existing patient to be uploaded to the medical network 150. For example, an existing patient seeking to upload a particular EOB to the medical network may scan the EOB using one or more input devices placed in wired or wireless communication with the existing patient client device 340. For instance, a camera system, recording device, scanning device or other input device capable of capturing the EOB as a digitized document and saving the digitized document to a computer readable storage device of the existing patient client device 340. The upload module 343 may load the digitized document into the memory of the existing patient client device 340 and transmit the digitized document from the existing patient client device 340 to the operation data system 302 for storage and/or the analytics processing system 301 for character recognition, cognitive analysis and tagging.

In some embodiments, the existing patient client device 340 may identify the context of each digitized document being uploaded to the medical network before transmitting the digitized document to one or more nodes 110 of the medical network 150. In order to perform the contextual analysis of each medical document selected for upload using the upload module 343, the user or the existing patient client device may provide context of the digitized document through the context augmentation interface 345. The context augmentation interface 345 may allow for the existing patient to apply additional metadata to the digitized document in order to more accurately process or query the digitized medical document in the future. For example, the context augmentation interface 345 may allow for an existing patient or the client device 340 to add context to the document by tagging the document with specific key words or fields, categorization of the document and applying location data describing the location where the services may have been provided.

In some embodiments, the context augmentation interface 345 may allow for the existing patient to amend the documents prior to being uploaded, creating an opportunity for the existing patient to add additional data that may not be present on a medical document such as an EOB or medical bill. For example, the existing patient may supplement the costs of the bill or EOB by adding estimated travel or lodging costs, an itemized and aggregated total costs for treating the injury or performing the procedure described by the document, rating the quality of the service provider, providing feedback and comments about the service provider, describing the outcome of the procedure and provide additional information about the insurance carrier and/or policy that covered the procedure. Once the additional context has been compiled onto the digitized document, the context augmentation interface 345 may save the document along with the updated context and notes provided by the existing patient. Subsequently, the copy of the amended digital document may be uploaded to the medical network and stored by the record management data store 325 and record of the uploaded document may be created or modified within the existing patient data store 321 and/or the existing patient profile 347.

Furthermore, the embodiment of the existing patient client device 340 may include a patient profile 347 which may be loaded into a memory device of the client device 340. The existing patient profile may store customized data and setting for the existing patient, including the patient's name, address, contact information, insurance provider, notification and contact preferences, reward status, upload history, default document privacy settings (i.e. default redaction of documents and visibility of contact information), login name and password authentication.

Referring to the drawings, FIG. 4 depicts an embodiment of an existing patient client device 340 displaying a thin client interface 405 such as through a web browser 403 or another software application capable of accessing a portal of the medical network 150. An existing patient accessing the medical network 150 using the client device 340 may authenticate the patient's right to access medical network 150 by logging in to the existing patient profile 347. Upon logging in via the web portal or application portal, the client interface 405 may display via the display device 401 of the client device 340, information stored by the existing patient profile 347, including the name of the existing patient or user, and the reward point status 409 of the patient.

In some embodiments of the existing patient client device 340, the interface 405 may actively engage the patient with system generated dialog 410 provided via the cognitive processing engine 310 and the AI natural language processor 311. As shown in the example of FIG. 4, the system generated dialog 410 may ask the patient how the system may assist the patient. Patients may choose to engage the medical network 150 by responding to the system generated dialog 410. For example, an existing patient may make a natural language input command 407 by speaking into a microphone or voice recording device connected to the client device 340 in some embodiments. In alternative embodiments, the existing patient may input a response using a keyboard or virtual keyboard provided on the interface 405. As shown in the example of FIG. 4, an existing patient may enter a command using a natural language input 407 indicating that the existing patient would like to share one or more medical documents with the medical network 150.

Figure 5:
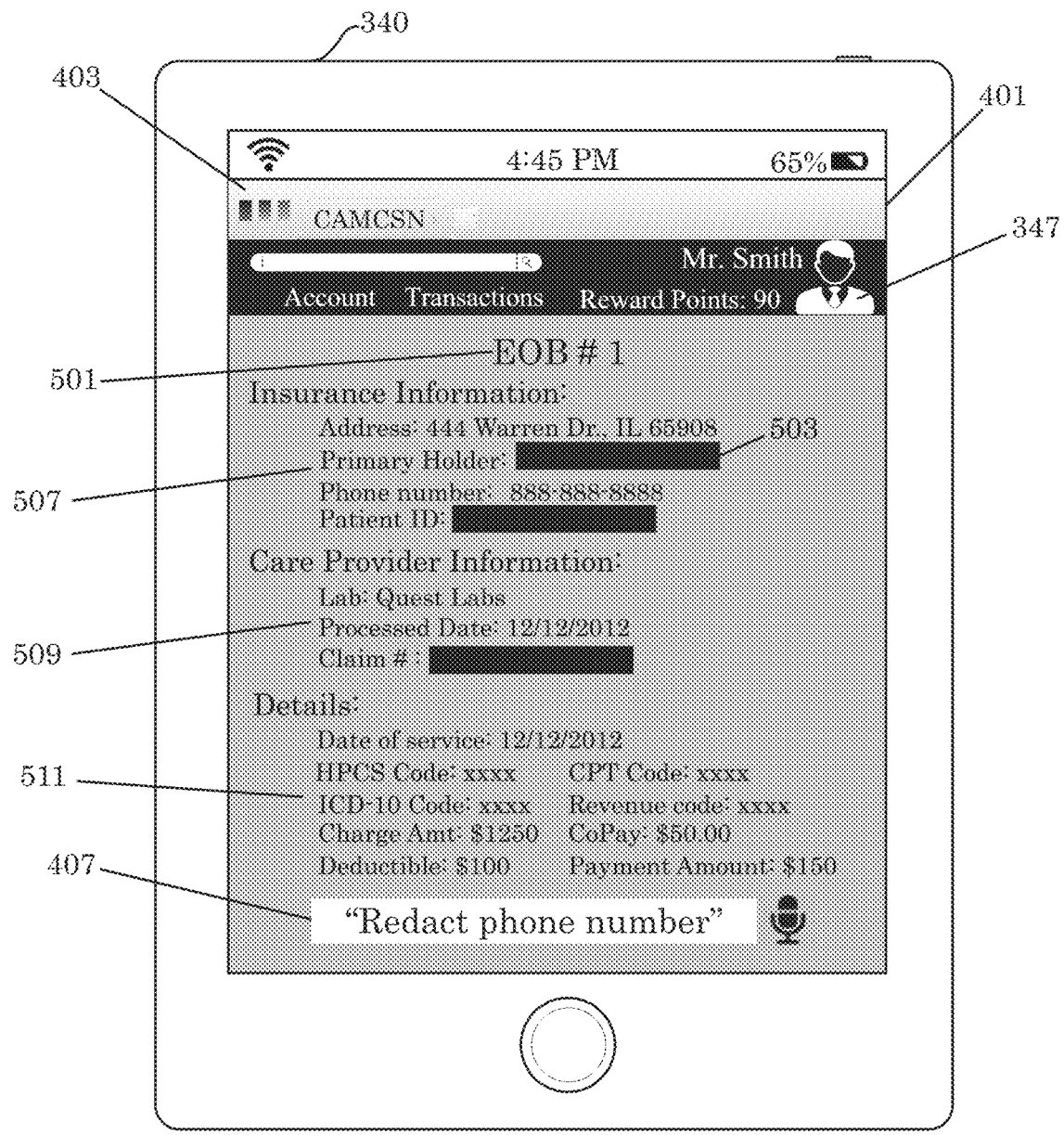
FIG. 5 illustrates an embodiment of an interface of a medical network inputting a natural language command to redact a shared medical document.

The embodiment of FIG. 5 depicts an example of an EOB scanned by the existing patient and displayed on the interface 405 of the existing patient client device 340. From the interface, the existing patient may add context to the EOB through the context augmentation interface and apply privacy measures to the document being prepared for upload to the medical network 150. Context augmentation, tagging, categorization, location information, redactions and additional modifications to the scanned document 501 may made using natural language input commands 407 directing the system 300 and more specifically the analytics processing system 301 to amend the scanned document 501.

For example, the scanned document may contain information that the existing patient may want to redact 503 in order to anonymize the existing patient so that confidentiality may be maintained. Descriptive user information may be present in various categories including insurance information 507 and care provider information 509. Items such as the name of the primary holder of the insurance, patient IDs, claim numbers patient names, addresses and phone numbers may be desirable to redact. As shown in FIG. 5, the existing patient may input natural language commands to redact 503 sensitive user information or may instruct the system 300 to apply default privacy settings prior to uploading the scanned document 501. Once the anonymization has been performed by the existing patient, the existing patient may instruct the upload module 343 to transmit the scanned document 501 to one or more nodes 110 connected to the medical network. Subsequently, as a function of uploading the scanned document 501, the existing patient's profile 347 may receive a reward from reward engine 315 for participating in the medical network 150 by helping to build the record management data store 325.

In some embodiments of system 300, one or more of the client devices 101 may be a prospective patient client device 330. Each prospective patient client device 330 may be any computing system, such as the generic computer system 1100 described in detail below. In addition to the generic computing elements such as the processor 1191, memory devices 1194, 1195 input devices 1192 and output devices 1193. The prospective patient client device 330 may comprise a medical network module 330. The medical network module 330 may be a hardware module or a software module comprising programming code loaded into a memory device of the existing patient client device 330. Embodiments of the medical network module 330 may include a guided search module 333, a results drill down module 335 and a prospective patient profile 337.

Embodiments of the guided search module 333 may perform the function or task of facilitating free form audio, speech and/or text input into the interface 405 of the medical network 150. The guided search module 333 may allow for the prospective patient to engage with the interface 405 of the medical network using a free-form, interview style dialog approach allowing for a back and forth of natural language input commands and responses with the cognitive processing engine 309. The guided search module 333 may allow for the prospective patient operating the prospective patient client device 330 to naturally speak into a microphone or other voice recording device to conduct a query of the records stored by the medical network 150 and the operation data system 302. Using natural language inputs, the prospective patient may define the search criteria and one or more values that may populate the fields of the medical documents being retrieved. The prospective patient may further use natural language to apply filters and/or weight various fields that may be present in the retrieved medical records allowing for the prioritized search results to be more customized to the specific search parameters authorized by the prospective patient. In alternative embodiments, a prospective patient may also use the guided search module 333 to input text into the interface 405 in order to communicate with the medical network 150 and the nodes 110 of the network 150.

In some embodiments of the system 300, the prospective patient client device 330 may further include a results drill down module 335 which may perform the function or task of organizing the query results returned by the analytics processing system by score, rank or prioritized matches. The results drill down module 335 may display the query results retrieved from the analytics processing system 301 and the operational data store 302 in a summarized format initially upon retrieval. However, a prospective patient may use the drill down module 335 to move deeper in the hierarchical structure of the search results to move on to more detailed data by clicking through the returned results all the way down to the specific file that may have been uploaded by the existing user. A prospective patient may drill down through the database of the record management data store and the search results to access information by starting with a general category and moving through the hierarchy of field to file to record.

Embodiments of the medical network module 331 may further include a prospective patient profile 337 which may store the preferences, settings and search history of the prospective patient as the prospective patient operates the client device 330. A prospective patient may alter the settings of the profile and set defaults to the profile 337 including acceptable systems for notifying the prospective patient, default query settings including specific search parameters such as cost, location, service provider, insurance carrier, etc. The prospective patient profile 337 may also include the reward status of the prospective patient's account, participating history and a detailed search history of the prospective patient's account.

Referring back to the drawings, FIGS. 6-9 provide an example of an interface 405 displayed by the prospective patient client device 330 performing a search of the medical network 150 for medical costs being shared by the medical network 150. As shown in FIG. 6, a prospective patient may access the interface 405 of the medical network via a thin client 403 or other application capable of accessing the medical network 150. The prospective patient may login to the prospective patient's profile 337. Once logged in, the interface 405 may generate system dialog 410a initiating the guided search performed by the guided search module 333. The prospective patient may respond to the initial system dialog 410a by responding using natural language inputs such as natural voice dialog inputted using a voice recording system or microphone in some embodiments. In other embodiments, the prospective patient may input text directly into the interface using a keyboard, virtual keyboard or other input device.

As shown in the exemplary embodiment of FIG. 6, a prospective patient may respond to the initial system dialog 410a with a natural language input 407a describing the patient's condition. In this particular example, the prospective patient describes the condition as a torn ACL, however, the prospective patient's condition could be any ailment or condition that may require medical assistance by a medical professional or medical service provider. The analytics processing system 301 may continue to respond and converse with the prospective patient through the interface 405. In the exemplary embodiment of FIG. 6, the analytics processing system 301 and more specifically, the cognitive processing engine 309 and the AI natural language processor 311 may generate an appropriate response dialog 410b. In this case prompting the prospective patient with a question of whether or not to query similar cases to the prospective patient's condition (the torn ACL).

In some embodiments of the system 300, the interface 405 may allow a prospective patient to further respond or refine the search criteria proposed in the response dialog 410b. As shown in FIG. 6, a prospective patient may describe additional search criteria with an additional natural language input 407b. For example, a prospective patient may prioritize certain fields of the query that are important to the prospective patient such as quality of service, price, wait time, and location of the available services.

In response to the search query proposed by the patient in FIG. 6 using natural language inputs, the analytics processing system may query the operational data system 302 and the record management data store 325 for the condition specified by the prospective patient. IN the particular example of FIG. 6, the analytics processing system 301 may search the record management system 325 for applicable torn ACL cases uploaded to the operational data system 302, analyze each of the records containing the queried condition and prioritize and additional parameters as requested by the prospective patient's natural language input command 407. In FIG. 7, an example of a prioritized search result is displayed by the display 401 of the prospective patient's client device 330.

As shown in FIG. 7, the prioritized search results may return a plurality of search results 701a, 701b which may be relevant to the search criteria of the prospective patient's query. Each of the returned results 701a, 701b may comprise a relevance score 703a, 703b describing how close to the query parameters each search result 701a, 701b has been determined to be by the cognitive processing engine 309 of the analytics processing system 301. The prioritized search results may be presented to the prospective patient with the most relevant result 701a first and decreasing the relevancy and the list of results descend. As shown in FIG. 7, the first result 701a contains the highest relevancy score 703a of 0.95 and is therefore presented above the next most relevant search result 701b, having a lower relevancy score 703b of 0.85.

Additional features displayed by the prioritized search results may include an option to contact 707 an existing patient linked to the search result or a service provider responsible for providing the services described by a particular search result 701a, 701b. Moreover, in some embodiments, a satisfactory search result may not be identified by the prospective patient based on the search criteria of the query. A prospective patient may modify or change the criteria of the query by inputting new or amended parameters, by either inserting text or via a natural language input command 407. As shown in FIG. 7, a prospective patient inputs a new command to expand the query by expanding the location of service providers beyond the scope of the immediate search, to neighboring locations.

Figure 8:
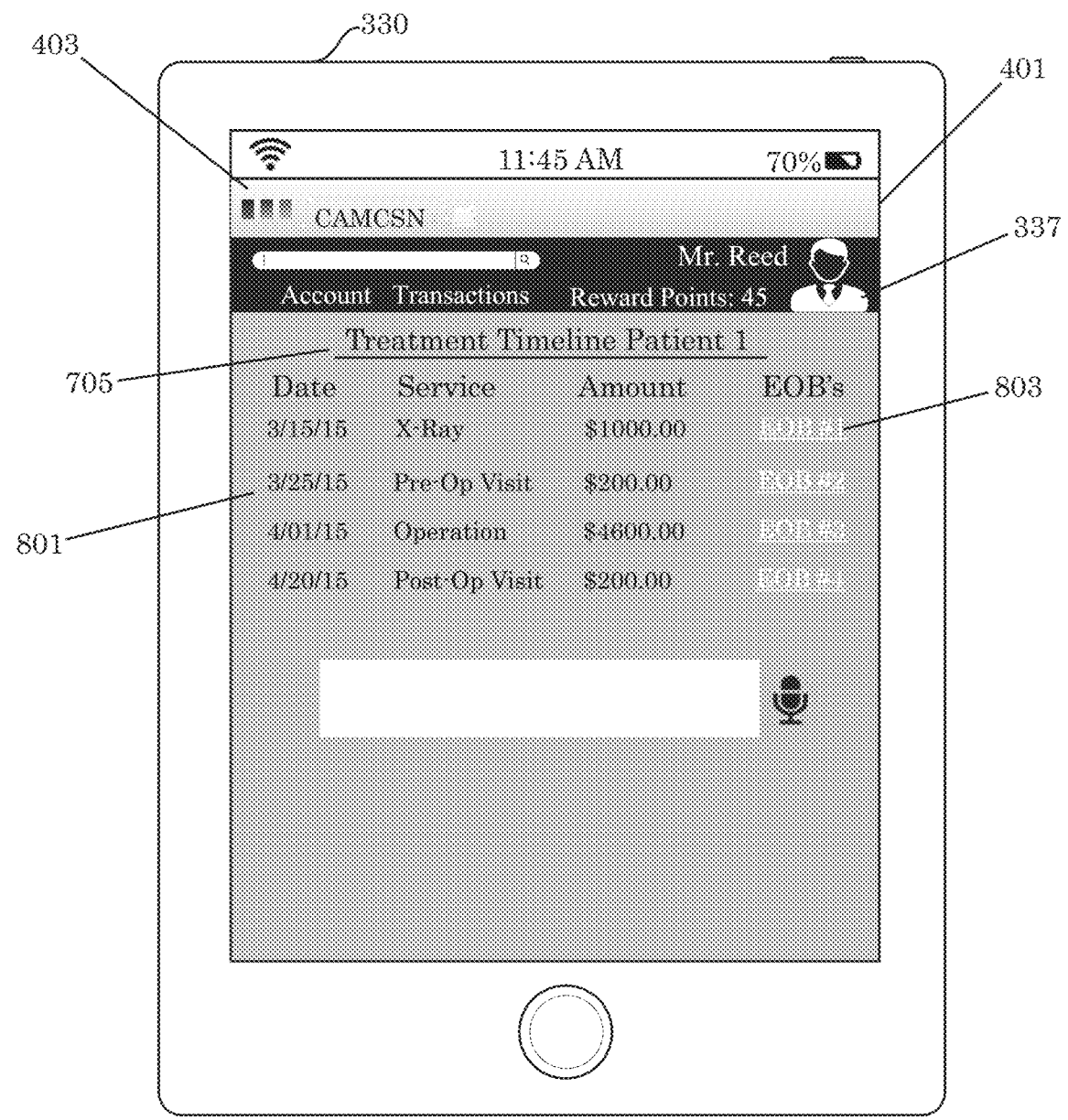
FIG. 8 illustrates an embodiment of an interface of a medical network displaying a timeline for treatment of a similar medical case returned by the prioritized search results of FIG. 7.

In some embodiments, the prospective patient may drill down deeper into the search results to obtain additional information via the results drill down module 335. As shown in FIG. 7, a prospective patient may access additional information from the search results, such as a link to a treatment timeline 705 of the existing patient that has provided the medical documents associated with the search result 701 selected by the prospective patient. A prospective patient may select the treatment timeline link 705 to drill down to the next level of information, as shown in FIG. 8. As shown in FIG. 8, the next level of the results drill down may be a detailed treatment timeline 705 describing one or more events 801 in the course of treatment experienced by the existing patient that shared the medical information. The treatment timeline 705 may include a summary of each event 801, including the date, service provided, the cost of each event 801 and an additional link to the medical document describing the event 801 of the timeline even further. In the particular example of FIG. 8, the treatment timeline 705 may include links to the specific medical documents uploaded to the medical network. In the specific example, the treatment timeline includes a plurality of EOBs containing links to the document's scanned image. In the example provided by FIG. 8-9, EOB #1 803 may be selected and upon selection, may be displayed by the display 401 of the prospective patient's client device 330 as the results are drilled down even further to the specific record of EOB #1.

Method for Sharing Medical Costs

Figure 10:
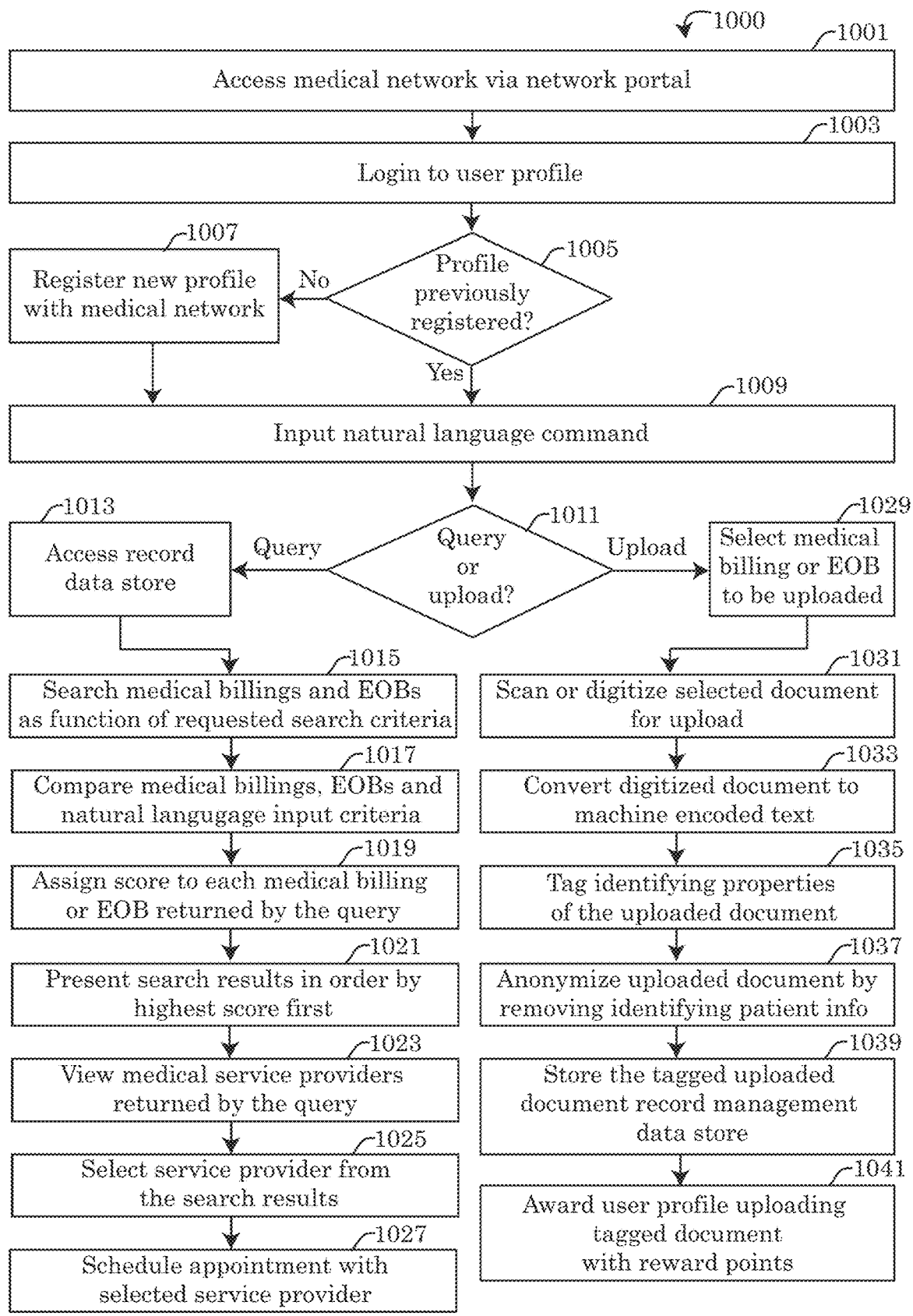
FIG. 10 depicts an embodiment of an algorithm for sharing medical costs to a medical network.

The drawing of FIG. 10 represents an embodiment 1000 of an algorithm that may be implemented for sharing medical costs within a medical network 150, in accordance with the systems described in FIGS. 1-9 using one or more computer systems defined generically in FIG. 11 below, and more specifically by the specific embodiments depicted in FIGS. 1-9. A person skilled in the art should recognize that the steps of the method described in FIG. 10 may not require all of the steps disclosed herein to be performed, nor does the algorithm of FIG. 10 necessarily require that all the steps be performed in the particular order presented. Variations of the method steps presented in FIG. 10 may be performed in a different order than presented by FIG. 10.

The algorithm 1000, described in FIG. 10, may initiate at step 1001 by a user or patient logging into the medical network 150 via a network portal in order to access the medical network 150. Access to the medical network 150 may be obtained from a client device 101, 301, 302 loading an application capable of connecting to the medical network or through the use of a thin client 403 such as a web browser. Once connected, the patient may in step 1003 login to the patient's user profile 337, 347 stored by the operational data system 302. A patient may login by presenting access credentials to the network 150. For example, a patient may login to the medical network using a login and password combination tied to the specific profile 337, 347 of the patient.

In step 1005, the system 300 may determine whether or not the profile 337, 347 has been previously registered to the patient. If the patient has not previously registered and/or it is the first time the patient is accessing the medical network 150, the algorithm may proceed to step 1007 wherein the patient may register a new profile 337,347 with the medical network 150 before proceeding to step 1009. Otherwise, if the patient is able to successfully log into a previously registered profile, the algorithm may proceed to step 1009.

In step 1009 of the algorithm 1000, a patient accessing the medical network 150 may input a natural language command 407 into the system 300. The natural language command 407 may be entered using a microphone or voice input device in some embodiments. In other embodiments, the natural language command may be written using an input device such as a keyboard, virtual keyboard, touchscreen or other input device. The natural language input may be unprompted in some instances or may be in response to system generated dialog 410 displayed by the patients' client device 101, 330, 340. In response to the natural language input 410, the system 100, 300 may provide a responding system generated dialog 410 or proceed with processing the natural language command 410.

In step 1011, the system 100, 300 may respond to the natural language command 410 inputted by the patient in step 1009 by making a determination as to the scope of the command. The algorithm 1000 may in some embodiments determine whether the natural language command is directed toward querying the records maintained by the system 100, 300 or contributing additional records to the system 100, 300 using the upload mechanism of an upload module 343. If, in step 1011, the patient's natural language command 410 is directed toward querying the records maintained by the system 100, 300, the algorithm may proceed to step 1013. Conversely, if the natural language command 410 is directed toward uploading or providing additional records to the system 100, 300 the algorithm may proceed to step 1013.

In step 1013, the algorithm 1000 may query the record management data store 325 of the operational data system 302, looking for records that match or closely match the search criteria of the query. In step 1015, the system 100, 300 may search medical billings, EOBs and the details of other medical records tagged with keywords and fields corresponding to the requested search criteria. In step 1017, the analytics processing system 301 may compare each of the fields of the records retrieved from the record management data store 325 with the natural language inputs provided by the patient. The analysis of the records retrieved may be performed by the AI natural language processor 311, the cognitive processing engine 309 and the scoring engine 313. Based on the analysis performed by the analytics processing system 301, the scoring engine 313, in step 1019 may assign a relevancy score 703 to each of the records, EOBs and/or medical documents retrieved from the record management data store 325.

In step 1021 of the algorithm 1000, the analytics processing system 301 may organize and present the search results of the query in step 1009 in a prioritized list which may be ordered according to the relevancy scores 703 assigned by the scoring engine 313. The prospective patient may, in step 1023 view the prioritized search results displayed on an interface 405 of the display 401 connected to the client device 330. The client device 330 may be directed by the prospective patient to drill down further into the results using the result drill down module 335 in order to obtain additional details of the search results. The prospective patient may view summaries of the search results, drill down one level to a treatment timeline 705 displaying a summary of a plurality of events 801 occurring as part of the treatment timeline 705. In some embodiments, the prospective patient may drill down even further into the search results and select individual EOBs 803 and display the documents scanned and uploaded by existing patients to the medical network 150.

Once the search results have been viewed in step 1023, a prospective patient may make an informed decision about the costs of treating a queried condition as a function of viewing past treatment costs from other patients that have treated the condition. In step 1025, the prospective patient may select a service provider associated with the treatment from one or more of the search results returned from the query in step 1021. The prospective patient may further proceed to contact and schedule an appointment to discuss or begin performing treatment of the condition in step 1027. In some embodiments, the scheduling step may be performed directly through the medical network 150. For example, a prospective patient may click a contact button 707 associated with the service provider or obtain the service provider contact information. In some embodiments, the service provider may be a member of the medical network 150 and may be directly messaged through the medical network messaging system.

Referring back to the determination step 1011, in some instances, the natural language input 407 may direct the system 100, 300 to upload one or more medical documents being provided by the existing patient of the medical network 150. The algorithm may proceed to step 1029, wherein the existing patient may select one or more medical bills, EOBs or other documents to be uploaded to the record management data store 325. In some embodiments, the medical documents selected for upload may be locally stored on the existing patient client device 340, whereas in alternative embodiments, the medical documents being uploaded may be remotely stored in a network accessible data store remotely accessible to client device 340.

In step 1031 of the algorithm 1000, the client device 340 may scan or digitize the documents selected for upload in step 1029. The scanning or digitization may be performed on hard copies of the documents being selected for upload. The documents may be converted into a digitized copy using scanning hardware such as a scanner or preparing an image of the selected document using a camera system. The camera or scanner system may be separate from the client device 340 or integrated into the hardware and/or software of the client device 340. Once scanned or digitized, the system 100, 300 may convert the digitized documents to machine encoded text in step 1033. Step 1033 may be performed via the character recognition module 307 allowing for the system 100, 300 to decipher the letters and numbers on the printed image of the documents and encode the image as machine readable text understood by the cognitive processing module 309 of the analytics processing system 301.

Once the text of the documents selected for uploading is placed into a machine readable text in step 1033, the algorithm may proceed to step 1035 wherein the cognitive processing engine and/or AI natural language processor 311 may tag identifying properties and fields of the documents scheduled to be uploaded to the operational data system 302. The analytics processing system 301 may further amend the Meta data of the file to include various keywords and descriptors of the file being uploaded and/or the values associated with the uploaded files in order to streamline and/or increase the query speed and accuracy of the system 100, 300. In some embodiments, the algorithm 1000 may further amend the documents scheduled for uploading by providing additional context, ratings, feedback etc. via the context augmentation interface. The additional augmentations created by the existing user may also be included during the tagging process of step 1035.

In some embodiments of the algorithm 1000, the documents scheduled to be uploaded to the record management store 325 of the operational data system 302 may be anonymized in step 1037. Anonymizing the documents may be performed as a default function in accordance with the privacy settings of the existing patient profile 347 or at the direction of the existing patient providing the documents as a function of a natural language input 407 instructing the system to redact sensitive or identifying information. Once the sensitive information has been redacted in accordance with the default privacy settings or at the direction of the existing patient providing the medical documents, the algorithm 1000 may proceed to step 1039. In step 1039, the uploaded documents that have been digitized and tagged may be stored by the system 100, 300 in the record management data store 325 and accessible to prospective patients who may query the system 100, 300.

Lastly, once the upload of the documents to the record management data store 325 has been completed in step 1039, the system 100, 300 may in step 1041 proceed to aware the existing patient uploading the tagged documents with rewards 409, such as points or other currency or discounts. The rewards 409 may be assigned by the rewards engine 315 once the uploaded documents have been verified by the rewards engine 315 as being saved to the record management data store 325.

Computer System

Figure 11:
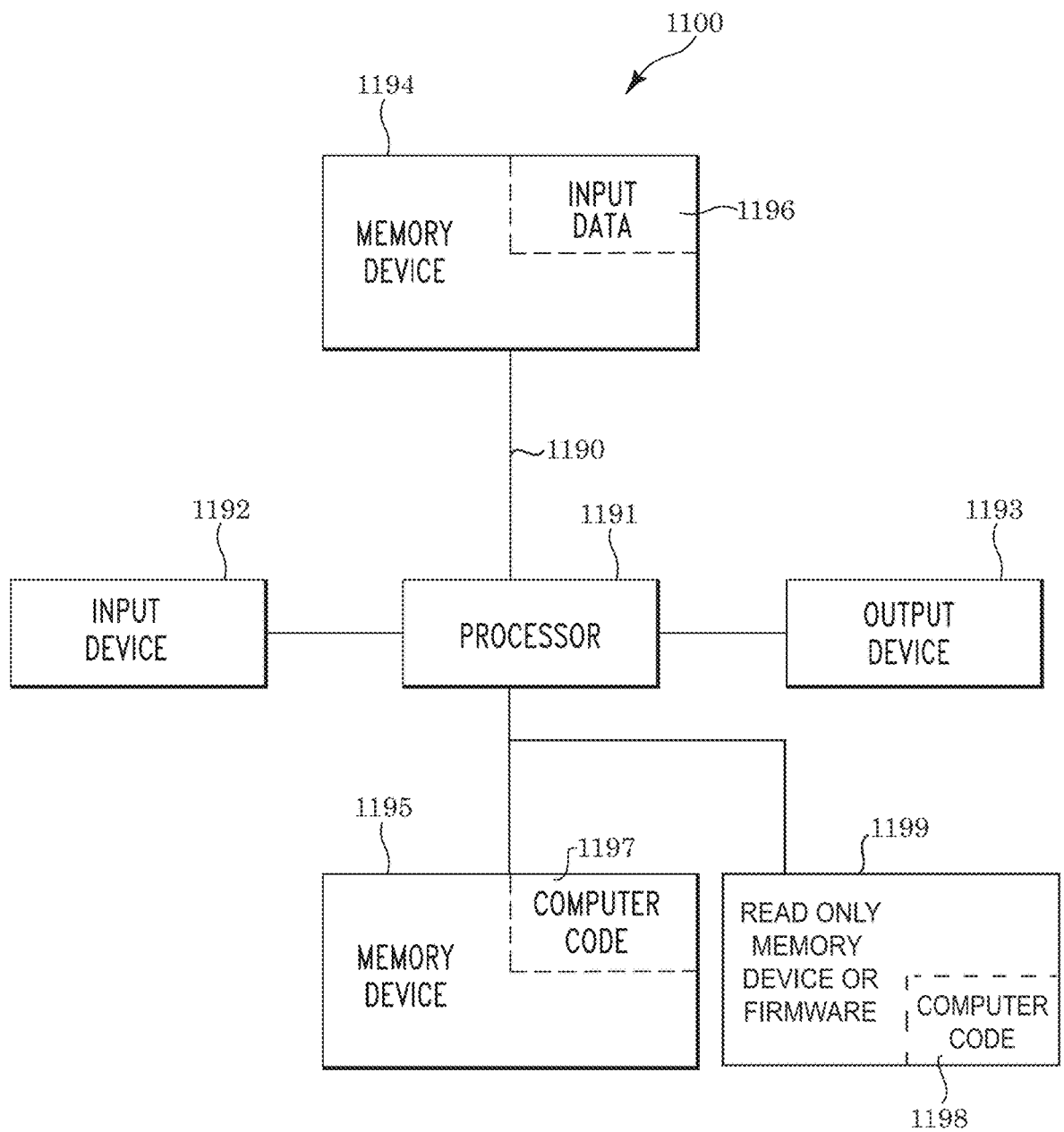
FIG. 11 depicts a block diagram of a computer system able to implement the methods for sharing medical costs to a medical network, consistent with the disclosure of the present application.

Referring to the drawings, FIG. 11 illustrates a block diagram of a computer system 1100 that may be included in the systems of FIGS. 1-9 and for implementing the methods for sharing medical costs with a medical network described in the algorithm of FIG. 10 and in accordance with the embodiments described in the present disclosure. The computer system 1100 may generally comprise a processor 1191, otherwise referred to as a central processing unit (CPU), an input device 1192 coupled to the processor 1191, an output device 1193 coupled to the processor 1191, and memory devices 1194 and 1195 each coupled to the processor 1191. The input device 1192, output device 1193 and memory devices 1194, 1195 may each be coupled to the processor 1191 via a bus 1190. Processor 1191 may perform computations and control the functions of computer 1100, including executing instructions included in the computer code 1197 for tools and programs for sharing medical costs with a medical network, in the manner prescribed by the embodiments of the disclosure using the systems of FIGS. 1-9 wherein the instructions of the computer code 1197 may be executed by processor 1191 via memory device 1195. The computer code 1197 may include software or program instructions that may implement one or more algorithms for implementing the methods for sharing medical costs with a medical network, as described in detail above and in FIG. 10. The processor 1191 executes the computer code 1197. Processor 1191 may include a single processing unit, or may be distributed across one or more processing units in one or more locations (e.g., on a client and server).

The memory device 1194 may include input data 1196. The input data 1196 includes any inputs required by the computer code 1197, 1198. The output device 1193 displays output from the computer code 1197, 1198. Either or both memory devices 1194 and 1195 may be used as a computer usable storage medium (or program storage device) having a computer readable program embodied therein and/or having other data stored therein, wherein the computer readable program comprises the computer code 1197, 1198. Generally, a computer program product (or, alternatively, an article of manufacture) of the computer system 1100 may comprise said computer usable storage medium (or said program storage device).

Memory devices 1194, 1195 include any known computer readable storage medium, including those described in detail below. In one embodiment, cache memory elements of memory devices 1194, 1195 may provide temporary storage of at least some program code (e.g., computer code 1197, 1198) in order to reduce the number of times code must be retrieved from bulk storage while instructions of the computer code 1197, 1198 are executed. Moreover, similar to processor 1191, memory devices 1194, 1195 may reside at a single physical location, including one or more types of data storage, or be distributed across a plurality of physical systems in various forms. Further, memory devices 1194, 1195 can include data distributed across, for example, a local area network (LAN) or a wide area network (WAN). Further, memory devices 1194, 1195 may include an operating system (not shown) and may include other systems not shown in the figures.

In some embodiments, rather than being stored and accessed from a hard drive, optical disc or other writeable, rewriteable, or removable hardware memory device 1194, 1195, stored computer program code 1198 (e.g., including algorithms) may be stored on a static, non-removable, read-only storage medium such as a Read-Only Memory (ROM) device 1199, or may be accessed by processor 1191 directly from such a static, non-removable, read-only medium 1199. Similarly, in some embodiments, stored computer program code 1197 may be stored as computer-readable firmware 1199, or may be accessed by processor 1191 directly from such firmware 1199, rather than from a more dynamic or removable hardware data-storage device 1195, such as a hard drive or optical disc.

In some embodiments, the computer system 1100 may further be coupled to an Input/output (I/O) interface (for example I/O interface 318) and a computer data storage unit (for example a data store, data mart or repository). An I/O interface may include any system for exchanging information to or from an input device 1192 or output device 1193. The input device 1192 may be, inter alia, a keyboard, joystick, trackball, touchpad, scanning device, bar code reader, mouse, sensors, beacons, RFID tags, microphones, recording device, biometric input device, camera, timer, etc. The output device 1193 may be, inter alia, a printer, a plotter, a display device (such as a computer screen or monitor), a magnetic tape, a removable hard disk, a floppy disk, etc. The memory devices 1194 and 1195 may be, inter alia, a hard disk, a floppy disk, a magnetic tape, an optical storage such as a compact disc (CD) or a digital video disc (DVD), a dynamic random access memory (DRAM), a read-only memory (ROM), etc. The bus 1190 may provide a communication link between each of the components in computer 1100, and may include any type of transmission link, including electrical, optical, wireless, etc.

The I/O interface may allow computer system 1100 to store information (e.g., data or program instructions such as program code 1197, 1198) on and retrieve the information from a computer data storage unit (not shown). Computer data storage units include any known computer-readable storage medium, which is described below. In one embodiment, computer data storage unit may be a non-volatile data storage device, such as a magnetic disk drive (i.e., hard disk drive) or an optical disc drive (e.g., a CD-ROM drive which receives a CD-ROM disk).

As will be appreciated by one skilled in the art, in a first embodiment, the present invention may be a method; in a second embodiment, the present invention may be a system; and in a third embodiment, the present invention may be a computer program product. Any of the components of the embodiments of the present invention can be deployed, managed, serviced, etc. by a service provider able to deploy or integrate computing infrastructure with respect to sharing medical costs with a medical network. Thus, an embodiment of the present invention discloses a process for supporting computer infrastructure, where the process includes providing at least one support service for at least one of integrating, hosting, maintaining and deploying computer-readable code (e.g., program code 1197, 1198) in a computer system (e.g., computer 1100) including one or more processor(s) 1191, wherein the processor(s) carry out instructions contained in the computer code 1197 causing the computer system to share medical costs with a medical network. Another embodiment discloses a process for supporting computer infrastructure, where the process includes integrating computer-readable program code into a computer system including a processor.

The step of integrating includes storing the program code in a computer-readable storage device of the computer system through use of the processor. The program code, upon being executed by the processor, implements a method for sharing medical costs with a medical network as described in this application. Thus the present invention discloses a process for supporting, deploying and/or integrating computer infrastructure, integrating, hosting, maintaining, and deploying computer-readable code into the computer system 1100, wherein the code in combination with the computer system 1100 is capable of performing a method of sharing medical costs with a medical network.

A computer program product of the present invention comprises one or more computer readable hardware storage devices having computer readable program code stored therein, said program code containing instructions executable by one or more processors of a computer system to implement the methods of the present invention.

A computer program product of the present invention comprises one or more computer readable hardware storage devices having computer readable program code stored therein, said program code containing instructions executable by one or more processors of a computer system to implement the methods of the present invention.

A computer system of the present invention comprises one or more processors, one or more memories, and one or more computer readable hardware storage devices, said one or more hardware storage devices containing program code executable by the one or more processors via the one or more memories to implement the methods of the present invention.

The present invention may be a system, a method, and/or a computer program product at any possible technical detail level of integration. The computer program product may include a computer readable storage medium (or media)

having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed:

1. A computer system, comprising: a processor; a memory device coupled to the processor; and a computer readable storage device coupled to the processor, wherein the storage device contains program code executable by the processor via the memory device to implement a method for sharing medical costs to a medical network, said method comprising:
converting, by the processor, text in a digitized explanation of benefits (EOB) document to machine encoded text, said EOB document pertaining to a previous medical treatment of an existing patient, said EOB document comprising fields of identifying properties of the EOB document, said identifying properties relating to the existing patient and to the medical treatment of the existing patient, said EOB document having been digitized after a natural language command had been inputted, said natural language command instructing an upload of the EOB document to a medical network, said natural language command having been inputted after a portal to the medical network was accessed;
after said converting, tagging, by the processor, the EOB document by generating identifiers for the fields in the EOB document that include the identifying properties of the EOB document and include the generated identifiers in the EOB document;
anonymizing, by the processor, confidential patient information provided within the EOB document by redacting the confidential patient information of the existing patient in the EOB document, said anonymizing not anonymizing a medical cost of the medical treatment in the EOB document;
uploading, by the processor, the tagged and anonymized EOB document to the medical network; and
receiving, by the processor, reward points in exchange for the tagged and anonymized EOB document uploaded to the medical network, said reward being compensation to the existing patient for making one or more properties of the identifying properties of the EOB document subsequently available to prospective patients.

2. The computer system of claim 1, said method further comprising:
inputting, by the processor, a natural language query command comprising information pertaining to a prospective patient's medical condition;
searching, by the processor using the natural language query command, a data store of the medical network for tagged documents uploaded to the medical network;
prioritizing, by the processor, results of the searching step; and
retrieving, by the processor, a prioritized list of the tagged documents, the tagged documents including a descriptor of a service performed and a price for performing the service performed including a descriptor of a service performed and a price for performing the service performed.

3. The computer system of claim 2, wherein said retrieving the results of the searching step comprises exchanging the reward points prior to viewing the prioritized list of tagged documents.

4. The computer system of claim 1, wherein said anonymizing the EOB document includes inputting a second natural language command instructing the computer system to redact a selected portion of the EOB document.

5. The computer system of claim 1, said method further comprising said storing the tagged EOB document to a data store of the medical network accessible to a plurality of members of the medical network, wherein the plurality of members of the medical network can download, retrieve or view the EOB document uploaded to the medical network.

6. The computer system of claim 2, wherein the prioritized list of tagged documents includes a link to a treatment timeline having a sorted list of a plurality of EOBs uploaded by a member of the medical network, and wherein the sorted list is sorted by date and includes a description of a treatment of a condition and costs for treating the condition from a start of the treatment of the condition to a conclusion of the treatment of the condition.

7. A computer program product comprising: one or more computer readable hardware storage devices having computer readable program code stored therein, said program code containing instructions executable by a processor of a computer system to implement a method for sharing medical costs to a medical network, said method comprising:
converting, by the processor, text in a digitized explanation of benefits (EOB) document to machine encoded text, said EOB document pertaining to a previous medical treatment of an existing patient, said EOB document comprising fields of identifying properties of the EOB document, said identifying properties relating to the existing patient and to the medical treatment of the existing patient, said EOB document having been digitized after a natural language command had been inputted, said natural language command instructing an upload of the EOB document to a medical network, said natural language command having been inputted after a portal to the medical network was accessed;
after said converting tagging, by the processor, the EOB document by generating identifiers for the fields in the EOB document that include the identifying properties of the EOB document and include the generated identifiers in the EOB document;
anonymizing, by the processor, confidential patient information provided within the EOB document by redacting the confidential patient information of the existing patient in the EOB document, said anonymizing not a medical cost of the medical treatment in the EOB document;
uploading, by the processor, the tagged and anonymized EOB document to the medical network; and
receiving, by the processor, reward points in exchange for the tagged and anonymized EOB document uploaded to the medical network, said reward being compensation to the existing patient for making one or more properties of the identifying properties of the EOB document subsequently available to prospective patients.

8. The computer program product of claim 7, said method further comprising:
inputting, by the processor, a natural language query command comprising information pertaining to a prospective patient's medical condition;
searching, by the processor using the natural language query command, a data store of the medical network for tagged documents uploaded to the medical network;
prioritizing, by the processor, results of the searching step; and
retrieving, by the processor, a prioritized list of the tagged documents, the tagged documents including a descriptor of a service performed and a price for performing the service performed including a descriptor of a service performed and a price for performing the service performed.

9. The computer program product of claim 8, wherein said retrieving the results of the searching step comprises exchanging the reward points prior to viewing the prioritized list of tagged documents.

10. The computer program product of claim 7, wherein said anonymizing the EOB document includes inputting a second natural language command instructing the computer system to redact a selected portion of the EOB document.

11. The computer program product of claim 7, said method further comprising said storing the tagged EOB document to a data store of the medical network accessible to a plurality of members of the medical network, wherein the plurality of members of the medical network can download, retrieve or view the EOB document uploaded to the medical network.

12. The computer program product of claim 8, wherein the prioritized list of tagged documents includes a link to a treatment timeline having a sorted list of a plurality of EOBs uploaded by a member of the medical network, and wherein the sorted list is sorted by date and includes a description of a treatment of a condition and costs for treating the condition from a start of the treatment of the condition to a conclusion of the treatment of the condition.

* * * * *